United States Patent
Scarberry et al.

(10) Patent No.: US 8,205,617 B2
(45) Date of Patent: Jun. 26, 2012

(54) ORAL APPLIANCE FOR TREATMENT OF SNORING AND SLEEP APNEA

(75) Inventors: Eugene N. Scarberry, Trafford, PA (US); Gary Lotz, Mars, PA (US); Lance Busch, Trafford, PA (US); Robert Dale Parks, Pittsburgh, PA (US); Christopher Stygar, Pittsburgh, PA (US); Ronald B. Kemnitzer, Blacksburg, VA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1105 days.

(21) Appl. No.: 11/801,994

(22) Filed: May 11, 2007

(65) Prior Publication Data
US 2007/0292819 A1 Dec. 20, 2007

Related U.S. Application Data

(60) Provisional application No. 60/813,405, filed on Jun. 14, 2006.

(51) Int. Cl.
*A61F 5/37* (2006.01)
*A61F 11/00* (2006.01)
*A61C 5/14* (2006.01)
*A61C 3/00* (2006.01)
*A61C 19/04* (2006.01)

(52) U.S. Cl. ........ 128/848; 128/846; 128/857; 128/859; 128/861; 128/862; 433/7; 433/68; 433/69

(58) Field of Classification Search ............. 128/200.26, 128/200.27, 207.12, 207.14, 207.15, 207.16, 128/846–848, 859–863; 433/7, 68, 69
See application file for complete search history.

(56) References Cited

U.S. PATENT DOCUMENTS

| | | | |
|---|---|---|---|
| 2,521,084 A | 9/1950 | Oberto | |
| 3,411,501 A | 11/1968 | Greenberg | |
| 3,878,610 A | 4/1975 | Coscina | |
| 4,255,138 A | 3/1981 | Frohn | |
| 4,350,154 A | 9/1982 | Feldbau | |
| 4,470,413 A | 9/1984 | Warncke | |
| 4,764,111 A | 8/1988 | Knierim | |
| 4,920,984 A | 5/1990 | Furumichi et al. | |
| 5,042,506 A | 8/1991 | Liberati | |
| 5,092,346 A | 3/1992 | Hays et al. | |
| 5,190,053 A | 3/1993 | Meer | |
| 5,245,592 A | 9/1993 | Kuemmel | |
| 5,365,945 A | 11/1994 | Halstrom | |
| 5,427,117 A | 6/1995 | Thornton | |
| 5,465,734 A * | 11/1995 | Alvarez et al. | 128/848 |
| 5,499,633 A | 3/1996 | Fenton | |
| 5,536,168 A | 7/1996 | Bourke | |
| 5,566,683 A | 10/1996 | Thornton | |

(Continued)

FOREIGN PATENT DOCUMENTS
WO  WO2007143624 A2   12/2007

*Primary Examiner* — Michael Brown
*Assistant Examiner* — Brandon Jackson

(57) ABSTRACT

An oral appliance is provided for the treatment of snoring and obstructive sleep apnea. The oral appliance includes an upper tray adaptable to conform to a user's maxillary dentition and a plurality of lower trays, each of the lower trays adaptable to conform to the user's mandibular dentition. At least some of the lower trays are structured to engage the upper tray, each of the lower trays are structured to impart a different fixed amount of mandibular advancement.

25 Claims, 22 Drawing Sheets

U.S. PATENT DOCUMENTS

| | | | | |
|---|---|---|---|---|
| 5,573,994 | A | 11/1996 | Kabra et al. | |
| 5,611,355 | A | 3/1997 | Hilsen | |
| 5,624,257 | A | 4/1997 | Farrell | |
| 5,642,737 | A | 7/1997 | Parks | |
| 5,678,567 | A | 10/1997 | Thornton et al. | |
| 5,752,510 | A | 5/1998 | Goldstein | |
| 5,755,219 | A | 5/1998 | Thornton | |
| 5,807,100 | A | 9/1998 | Thornton | |
| 5,829,441 | A | 11/1998 | Kidd et al. | |
| 5,868,138 | A | 2/1999 | Halstrom | |
| 5,954,048 | A | 9/1999 | Thornton | |
| 6,012,455 | A | 1/2000 | Goldstein | |
| 6,041,784 | A | 3/2000 | Halstrom | |
| 6,129,084 | A | 10/2000 | Bergensen | |
| 6,161,542 | A | 12/2000 | Halstrom | |
| 6,170,485 | B1 * | 1/2001 | Orrico | 128/848 |
| 6,212,435 | B1 * | 4/2001 | Lattner et al. | 607/134 |
| 6,247,926 | B1 | 6/2001 | Thornton | |
| 6,405,729 | B1 | 6/2002 | Thornton | |
| 6,435,870 | B1 | 8/2002 | Walde | |
| 6,450,167 | B1 | 9/2002 | David et al. | |
| 6,516,805 | B1 | 2/2003 | Thornton | |
| 6,584,978 | B1 | 7/2003 | Brett et al. | |
| 6,618,627 | B2 * | 9/2003 | Lattner et al. | 607/134 |
| 6,729,335 | B1 | 5/2004 | Halstrom | |
| 6,789,543 | B2 | 9/2004 | Cannon | |
| 6,877,513 | B2 * | 4/2005 | Scarberry et al. | 128/848 |
| 7,021,312 | B2 | 4/2006 | Cannon | |
| 7,802,987 | B1 * | 9/2010 | Phan | 433/24 |
| 2003/0217753 | A1 | 11/2003 | Thornton | |
| 2004/0099275 | A1 * | 5/2004 | Zacco | 128/848 |
| 2007/0074729 | A1 | 4/2007 | Magnin | |

* cited by examiner

ORAL APPLIANCE FOR TREATMENT OF SNORING AND SLEEP APNEA

CROSS-REFERENCE TO RELATED APPLICATIONS

This application claims priority under 35 U.S.C. §119(e) from provisional U.S. patent application No. 60/813,405 filed Jun. 14, 2006 the contents of which are incorporated herein by reference.

BACKGROUND OF THE INVENTION

1. Field of the Invention

The present invention pertains to an oral appliance and more particularly to an oral appliance for the treatment of snoring and sleep apnea.

2. Description of the Related Art

Individuals suffering from sleep-related breathing disorders, such as excessive snoring and sleep apnea, have an increased risk of experiencing severe health problems. Studies have shown, for instance, that individuals suffering from obstructive sleep apnea (OSA) are more likely to have a stroke, heart failure, hypertension, and depression, among others. OSA is characterized by repetitive collapse of the upper airway during sleep. This yields episodes of reduced airflow, hypoxemia (reduced oxygen level in the blood), hypercapnia (elevated circulating carbon dioxide, $CO_2$), and arousal from sleep to reestablish a stable airway.

Severe sleep-related breathing disorders may require positive airway pressure (PAP) therapy. Less severe sleep-related breathing disorders, however, may be treated with other therapies or devices, such as an oral appliance. Generally, an oral appliance includes upper and lower dental trays coupled together in such a way as to impart forward advancement of the user's mandible (i.e., lower jaw) relative to the user's maxilla (upper jaw). Accordingly, an oral appliance may also be referred to as a "mandibular advancement device" or "MAD". Forward advancement of the mandible helps prevent the soft tissue of the tongue and the throat from collapsing into, and thus blocking, the user's airway during sleep.

Achieving the correct amount of forward mandibular advancement with an oral appliance is important. A user, for example, may continue to suffer from a sleep-related breathing disorder if the forward mandibular advancement imparted by the oral appliance is inadequate (e.g., the soft tissue of the user's tongue and throat are not prevented from collapsing into the user's airway). On the other hand, if the forward mandibular advancement imparted by the oral appliance is excessive, the user may experience unnecessary discomfort. The discomfort may cause undesirable arousal from sleep and/or cause the user to stop wearing the oral appliance all together.

Some oral appliances, such as those described in U.S. Pat. Nos. 5,829,441, 5,365,945, and 5,868,138, include mechanisms for adjusting the amount of mandibular advancement provided by the oral appliance. These and similar oral appliances, however, are expensive, complicated to manufacture, and have adjustment mechanisms are difficult to operate. Additionally, oral appliances incorporating adjustment mechanisms tend to be bulky, thereby adversely impacting the user's comfort level. Furthermore, known oral appliances are difficult to properly fit, do not allow sufficient vertical or horizontal movement of the jaw when worn, and are not flexible enough to allow a "one size fits all" application (e.g., the oral appliance may not be appropriate for both a user having a relatively small dental arch and a user having a relatively large dental arch).

Accordingly, a need exists for an improved oral appliance for the treatment of snoring and sleep apnea which overcomes these and other problems associated with known oral appliances.

SUMMARY OF THE INVENTION

In accordance with an aspect of the present invention, an oral appliance system comprises an upper tray and a plurality of lower trays. The upper tray is adaptable to conform to a user's maxillary dentition and each of the lower trays is adaptable to conform to the user's mandibular dentition. The lower trays are structured to engage the upper tray and each of the lower trays is structured to impart a different fixed amount of mandibular advancement and/or different amount of vertical height.

According to another aspect of the present invention, an oral appliance tray comprises a moldable material and a support member. The moldable material includes a channel structured to align a user's dentition within the center thereof. The channel has a substantially V-shaped portion structured to engage an anterior portion of a user's dentition and a substantially U-shaped portion structured to engage a posterior portion of the user's dentition. The support member is structured to carry the moldable material thereon.

According to another aspect of the present invention, an oral appliance tray comprises a moldable material and a support member. The support member has a base, an outer wall, and an inner wall which define a region adapted to couple with the moldable material. A portion of the moldable material may extend out of the region.

According to another aspect of the present invention, an oral appliance tray comprises a moldable material and a support member structured to carry a portion of the moldable material. The support member has a ramp adapted to promote alignment of a user's dentition relative to the moldable material.

According to another aspect of the present invention, an oral appliance assembly comprises an oral appliance tray adaptable to conform to a user's dentition and a holding tray adapted to promote proper insertion of the oral appliance tray into a user's mouth. The holding tray comprises a generally U-shaped frame structured to couple with the oral appliance tray and a handle located substantially at the vertex of the holding tray frame.

According to another aspect of the present invention, a method for effecting the patency of a user's airway comprises providing an oral appliance assembly comprising an upper tray adaptable to conform to a user's maxillary dentition and a plurality of lower trays each adaptable to conform to the user's mandibular dentition, wherein each of at least some of the lower trays is structured to couple with the upper tray to impart a different fixed amount of mandibular advancement, enabling a selection of at least one of the plurality of lower trays, and enabling coupling of the upper tray with a selected one of the lower trays to form an oral appliance having a desired amount of mandibular advancement.

According to another aspect of the present invention, an oral appliance tray comprises a generally U-shaped support member having a first width relative to a vertex thereof that is between approximately 0.30 inches (7.62 millimeters) and approximately 0.53 inches (13.46 millimeters) and having a second width relative to at least one of a first leg and a second leg thereof that is between approximately 0.50 inches (12.7 millimeters) and approximately 0.73 inches (18.54 millimeters).

According to another aspect of the present invention, a holding tray adapted to promote proper insertion of an oral appliance into a user's mouth comprises a generally U-shaped frame and a handle. The frame is structured to engage the oral appliance and has a base with an outer wall extending therefrom. The handle, projecting from a front surface of the outer wall, is substantially located at the vertex of the U-shaped frame.

According to another aspect of the present invention, a method for fitting an oral appliance comprises taking an impression of a user's dentition, creating a casting of the user's dentition using the impression, heating the casting to a predetermined temperature, and placing the heated casting in an oral appliance having a moldable material.

According to another aspect of the present invention, a method for fitting an oral appliance comprises enabling an oral appliance tray to couple with a holding tray, the oral appliance tray having a moldable material and the holding tray having a handle, enabling the oral appliance tray to be submerged within a heating medium without submerging at least a portion of the handle, enabling removal of the oral appliance tray from the heating medium using the handle, enabling insertion of the oral appliance tray into a user's mouth using the handle, and enabling the user to make an impression of a portion of the user's dentition.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
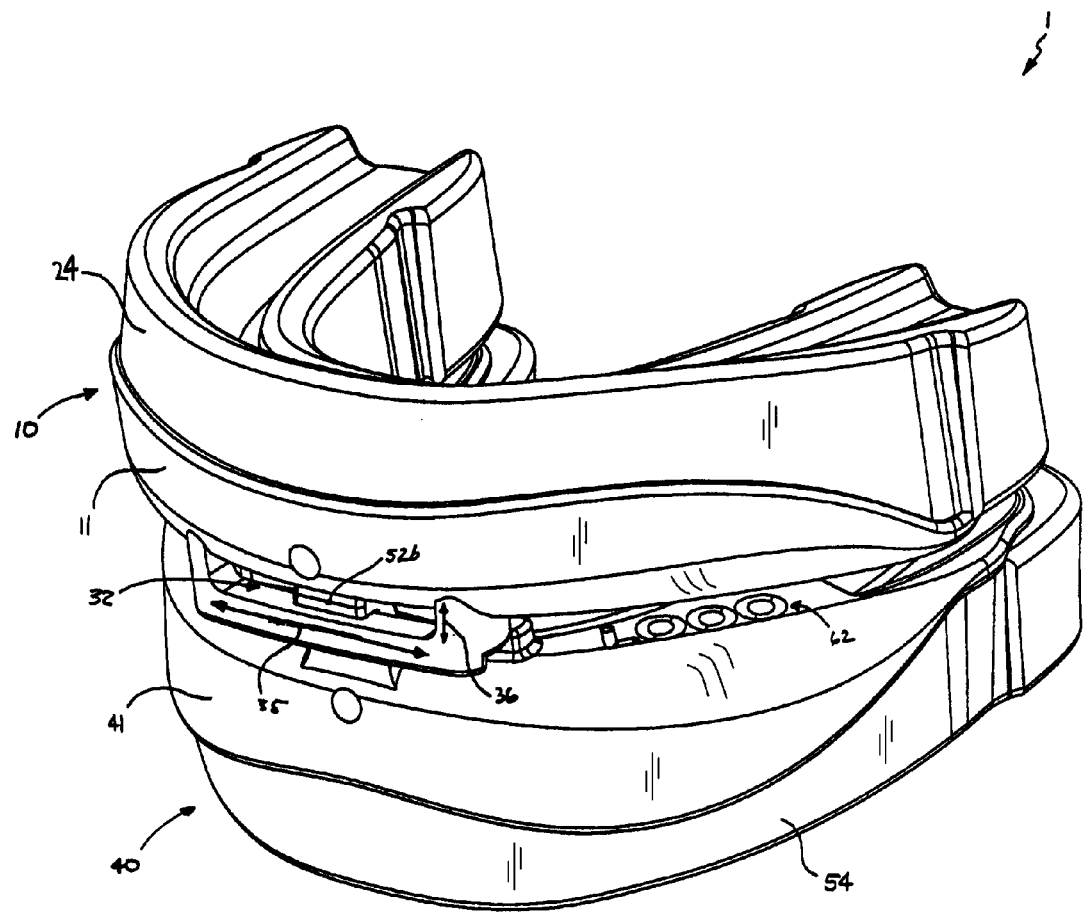
FIG. 1 is a perspective view of an oral appliance according to one embodiment.
Figure 2:
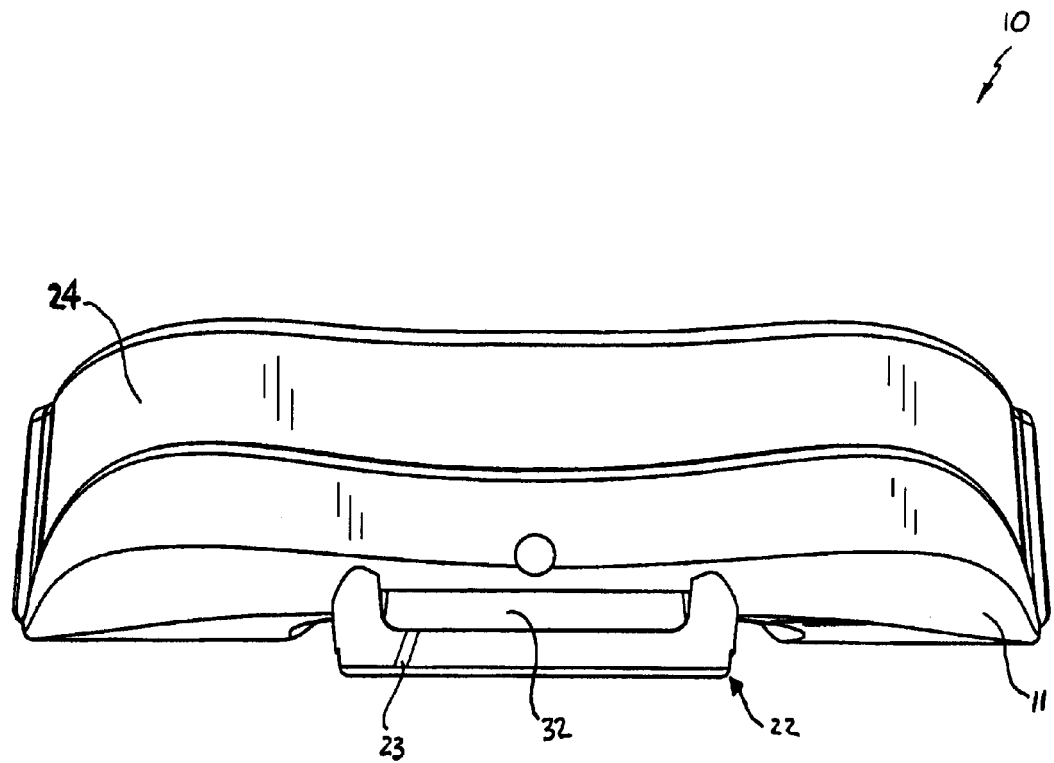
FIG. 2 is a front plan view of the upper tray for the oral appliance illustrated in FIG. 1.

Directional phrases used herein, such as, for example, left, right, clockwise, counterclockwise, top, bottom, up, down, and derivatives thereof, relate to the orientation of the elements shown in the drawings and are not limiting upon the claims unless expressly recited therein.

As employed herein, the term "number" shall mean one or more than one and the singular form of "a", "an", and "the" include plural referents unless the context clearly indicates otherwise.

As employed herein, the statement that two or more parts are "connected" or "coupled" together shall mean that the parts are joined together either directly or joined together through one or more intermediate parts. Further, as employed herein, the statement that two or more parts are "attached" shall mean that the parts are joined together directly.

As employed herein, the term "mandibular advancement" and derivatives thereof refer to the anterior movement of a user's mandible (lower jaw) relative to the user's maxilla (upper jaw). Lateral movement, as employed herein, refers to the left/right movement of the mandible relative to a sagittal plane passing through the interproximal space of the maxillary centrals. Vertical movement, as employed herein, refers to an increase/decrease of the spacing between the occlusal surfaces of the mandibular dentition and the occlusal surfaces of the maxillary dentition.

An oral appliance 1 according to one embodiment is shown in FIG. 1. The oral appliance 1 includes an upper tray 10 adaptable to conform to a user's maxillary dentition and a lower tray 40 adaptable to conform to the user's mandibular dentition. Although only one lower tray 40 is illustrated in FIG. 1, it is contemplated that multiple lower trays 40 will be provided. As will be discussed in more detail below, each of at least some of the multiple lower trays 40 is structured to impart a different fixed amount of mandibular advancement when engaged with upper tray 10. A lower tray 40 may also be structured to provide, in combination with upper tray 10, a fixed amount of vertical spacing between the user's maxillary dentition and mandibular dentition. Accordingly, a user and/ or dental specialist may select the proper lower tray 40 to provide a desired amount of mandibular advancement and/or a desired amount of vertical spacing.

FIGS. 2-5 are front, bottom, top, and side plan views of upper tray 10 for oral appliance 1 of FIG. 1. Upper tray 10 is generally U-shaped (e.g., having two legs 16b, 16c extending from a vertex 16a). Upper tray 10 includes an upper support member 11 and an upper moldable material 24.

Figure 3:
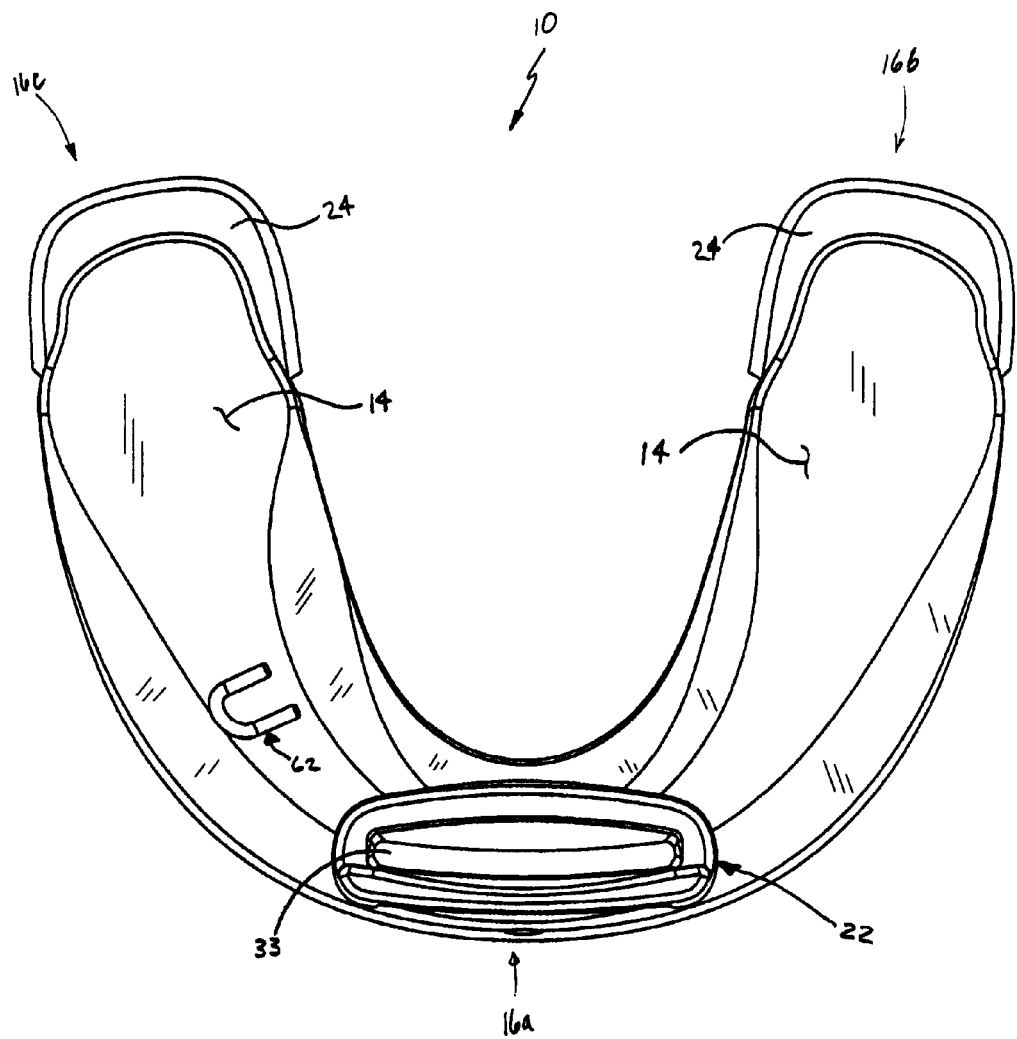
FIG. 3 is a bottom plan view of the upper tray illustrated in FIG. 2.
Figure 6:
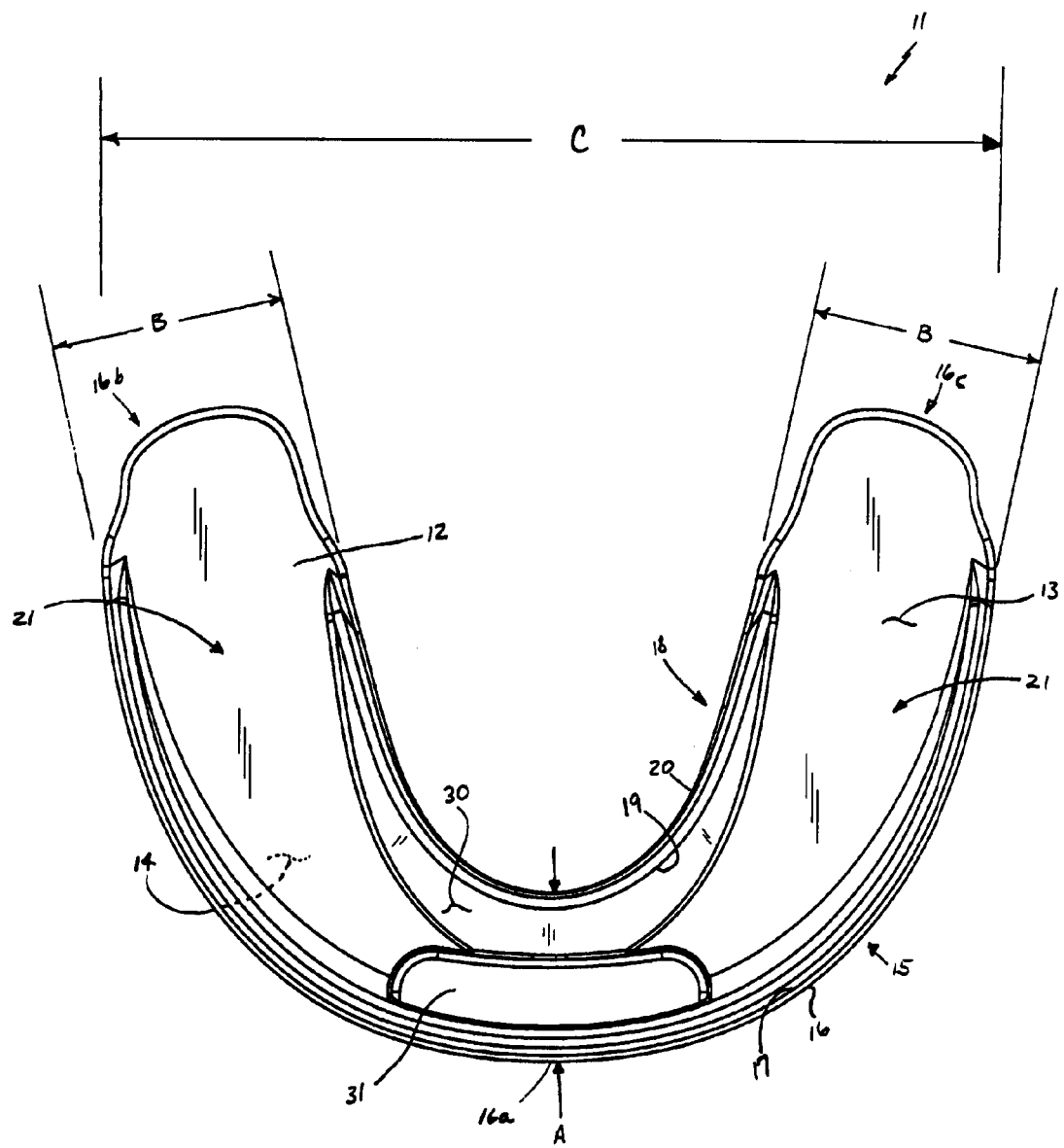
FIG. 6 is a top plan view of the upper support member portion of the upper tray illustrated in FIG. 2.
Figure 7:
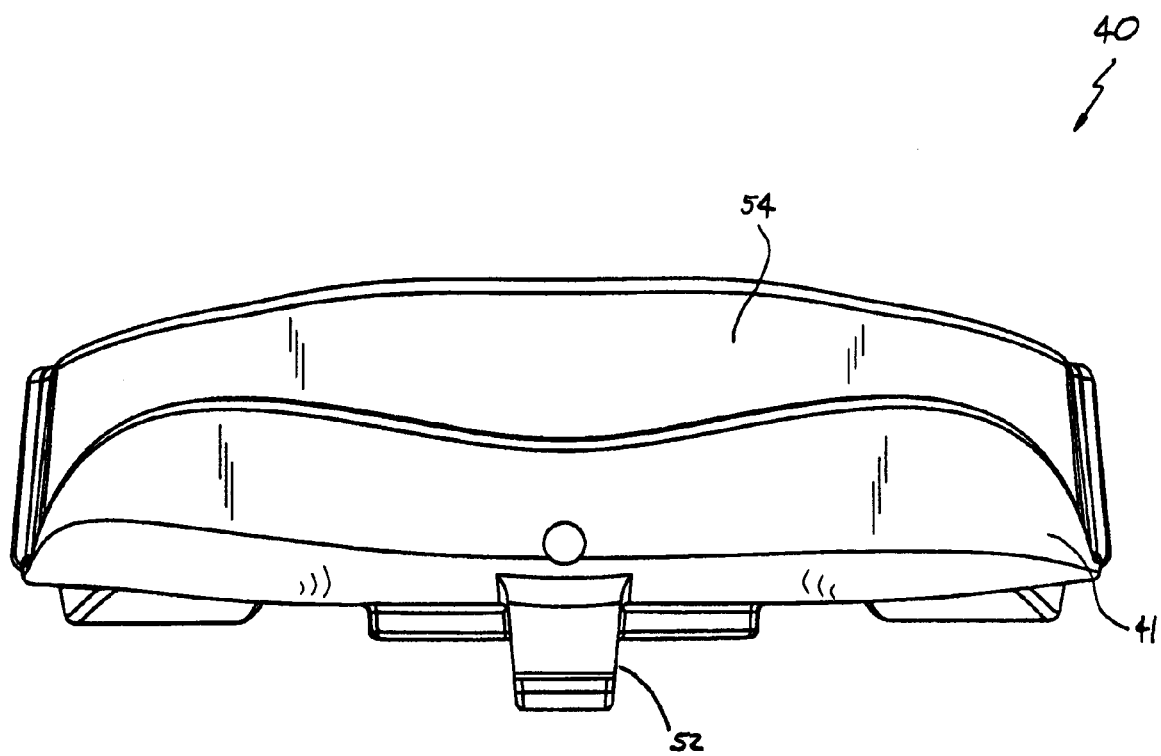
FIG. 7 is a front plan view of the lower tray for the oral appliance illustrated in FIG. 1.

A top plan view of upper support member 11 without upper moldable material 24 coupled thereto, for one embodiment, is illustrated in FIG. 6. Upper support member 11 has a base 12 with a bonding surface 13 and an occlusal surface 14, an outer wall 15 with a front surface 16 and a rear surface 17, and an inner wall 18 with a front surface 19 and a rear surface 20. A single slotted engagement member 22 (FIG. 3) extends from occlusal surface 14. A ramp 30 slopes downwardly from the top of a portion of inner wall 18 to a shelf 31 on bonding surface 13. As will be discussed in greater detail below, ramp 30 is structured to assist with centering the user's dentition relative to tray 10 during fitting while shelf 31 is structured to help provide the desired vertical spacing between the patient's maxillary and mandibular dentition. Upper support member 11 may include identification markings 62. In the current embodiment, for example and without limitation, upper support member 11 includes the letter "U" on occlusal surface 14 (FIG. 3).

Traveling from leg 16b to leg 16c along base 12, bonding surface 13 generally lies on a single plane (i.e., bonding surface 13 is generally flat). In an alternative embodiment, however, it is contemplated that bonding surface 13 may be somewhat curved in order to better accommodate the Curve of Spee associated with a user's dentition. Specifically, it is contemplated that bonding surface 13 is somewhat concave to accommodate the convex Curve of Spee associated with a user's maxillary dentition.

Generally, upper support member 11 has a first width (A) at vertex 16a that is between approximately 0.30 inches (7.62 millimeters) and approximately 0.53 inches (13.46 millimeters). Upper support member 11 also has, relative to at least one of first leg 16b and second leg 16c, a second width (B) that is between approximately 0.50 inches (12.70 millimeters) and approximately 0.73 inches (18.54 millimeters). The distance between the outer portion of first leg 16b and the outer portion of second leg 16c is a third width (C) that is between approximately 2.0 inches (50.8 millimeters) and approximately 2.80 inches (71.12 millimeters). In the current embodiment, first width (A) is approximately 0.41 inches (10.41 millimeters), second width (B) is approximately 0.60 inches (15.24 millimeters), and third width (C) is approximately 2.27 inches (57.66 millimeters).

Upper support member 11 is sized such that the ratio between first width (A) and second width (B) is between approximately 0.60 and approximately 0.73 and the ratio between first width (A) and third width (C) is between approximately 0.17 and approximately 0.19. In the current embodiment, for example, the ratio between first width (A) and second width (B) is approximately 0.68 and the ratio between first width (A) and third width (C) is approximately 0.18.

Figure 5:
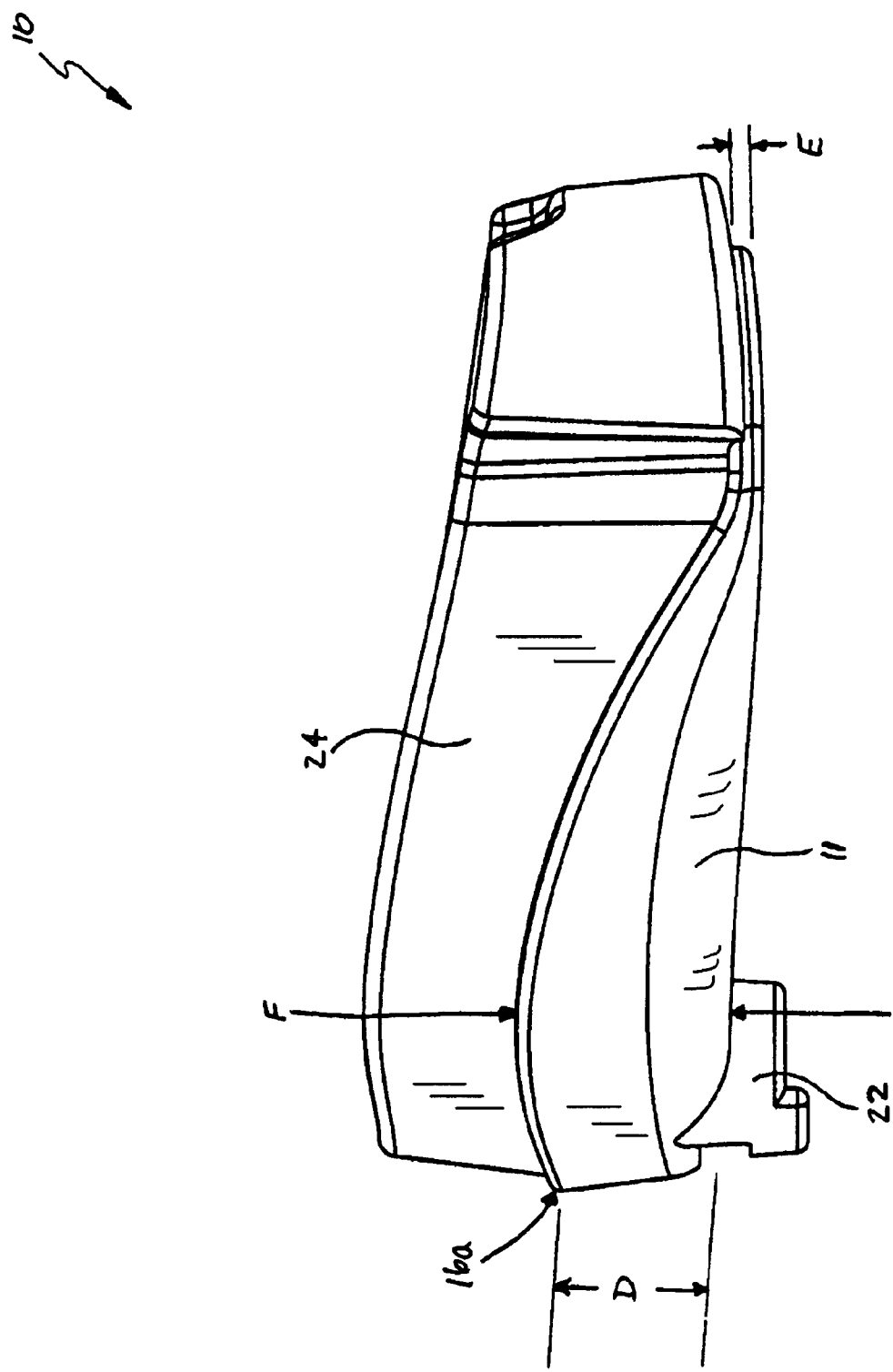
FIG. 5 is a side plan view of the upper tray illustrated in FIG. 2.

Referring briefly to FIG. 5, upper support member 11 has, relative to vertex 16a, a first height (D) that is between approximately 0.30 inches (7.62 millimeters) and approximately 0.50 inches (12.70 millimeters), and has a second height (E) relative to at least one of a first leg 16b and a second leg 16c that is between approximately 0.025 inches (0.635 millimeters) and approximately 0.42 inches (10.67 millimeters). In the current embodiment, first height (D) and second height (E) are selected such that the ratio between second height (E) and first height (D) is between approximately 0.083 and approximately 0.125. Furthermore, upper support member 11 has a maximum height (F) that is approximately between 0.30 inches (7.62 millimeters) and 0.48 inches (12.19 millimeters).

In the current embodiment, first height (D) is approximately 0.31 inches (7.87 millimeters), second height (E) is approximately 0.032 inches (0.813 millimeters), the ratio between second height (E) and first height (D) is approximately 0.10, and maximum height (F) is approximately 0.37 inches (9.40 millimeters).

Upper support member 11 may be constructed of any rigid or semi-rigid material suitable for dental use. In the current embodiment, upper support member 11 has a density that is approximately between 0.040 lb/in3 and 0.050 lb/in$^3$, a volume that is between approximately 0.12 in$^3$ and 0.22 in$^3$ and a weight that is between approximately 0.0071 lbs and 0.0081 lbs. For example, upper support member 11 is constructed of a polycarbonate resin thermoplastic, such as LEXAN, and has a density of approximately 0.045 lb/in$^3$, a volume of approximately 0.17 in$^3$, and a weight of approximately 0.0076 lbs.

Returning to FIG. 6, upper support member 11 defines an upper region 21. Upper region 21 is generally defined, for example and without limitation, by base bonding surface 13, outer wall rear surface 17, and inner wall front surface 19. Upper region 21 is adapted to carry a portion of upper moldable material 24 therein. Upper moldable material 24 may be coupled to upper support member 11 in any suitable manner, for example and without limitation, using an adhesive.

Upper moldable material 24 is not restricted within upper region 21. As seen for example in FIGS. 2, 3, and 5, at least a portion of moldable material 24 extends out of upper region 21. In the current embodiment, it is contemplated that a portion of upper moldable material 24 extends at least 0.00984 inches (0.25 millimeters) above outer wall rear surface 17, at least 0.0256 inches (0.65 millimeters) above inner wall front surface 19, and at least 0.00394 inches (0.1 millimeters) from the end of bonding surface 13 of base 12 (i.e., from the end of the legs 16b, 16c of upper support member 11). It should be noted that the amount that moldable material 24 extends out of any portion of upper region 21 may be varied while remaining within the scope of the present invention.

A moldable material may be selected which yields when heated, thereby conforming to the user's dentition during fitting, and re-hardens when cooled, thereby retaining the shape of the user's dentition imparted during fitting. Such a moldable material is sometimes referred to as a "boil and bite" material. In the current embodiment, for example, moldable material 24 is an ethylene-vinyl acetate copolymer resin, such as ELVAX, having a density of approximately 0.035 lb/in$^3$, a volume of approximately 0.75 in$^3$, and a weight of approximately 0.0263 lbs.

Oral appliance 1 incorporating an upper tray 10 provides benefits over other oral appliances which have an upper tray comprised solely of a moldable material or comprised of a moldable material which is substantially completely contained within a support member. For example, upper support member 11 is smaller than other upper support members which completely enclose their moldable material. Furthermore, by allowing a portion of upper moldable material 24 to extend out from upper support member 11, upper tray 10 is better able to conform to the user's maxillary dentition during the fitting process. More specifically, moldable material 24 is afforded a greater range of flow allowing moldable material 24 to conform to the user's dentition even if the user's dentition includes one or more misaligned teeth. Moldable material 24, such as that extending from the end of bonding surface 13, can be manipulated during the fitting process to conform to the user's dentition. Additionally, unlike other oral appliances which are comprised solely of a moldable material, upper support member 11 provides additional support to moldable material 24 during and after the fitting process. For these and other reasons, upper support member 11 provides increased patient comfort and allows upper tray 10 to fit a greater range of dental arch sizes.

Figure 4:
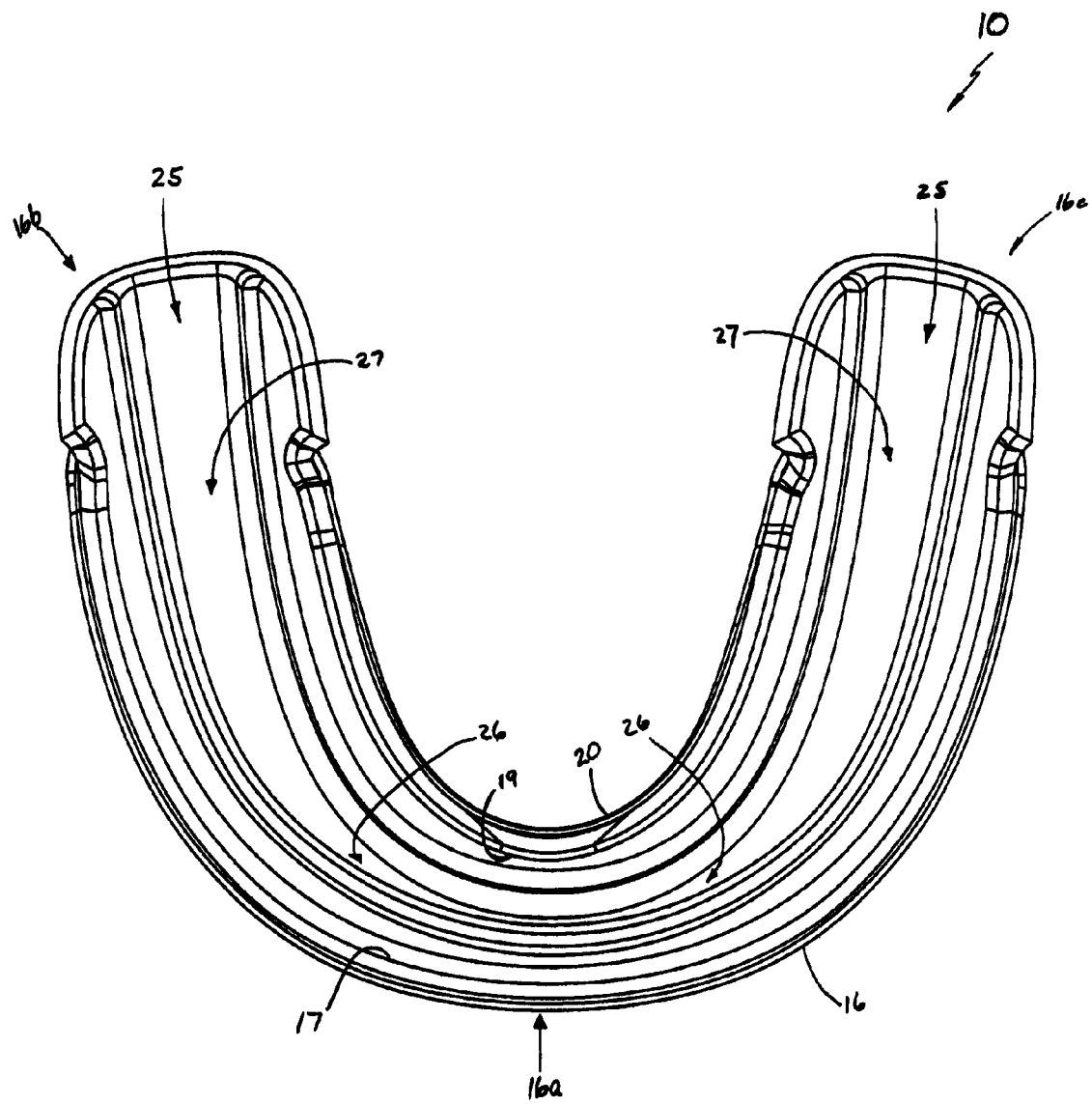
FIG. 4 is a top plan view of the upper tray illustrated in FIG. 2.

Referring now to FIG. 4, upper moldable material 24 has a channel 25 structured to center a user's dentition therein. More specifically, channel 25 includes a substantially V-shaped portion 26 structured to engage an anterior portion of the user's maxillary dentition (e.g., the upper centrals, laterals, and cuspids) and a substantially U-shaped portion 27 structured to engage a posterior portion of the user's maxillary dentition (e.g., the upper bicuspids and molars). By centering the user's upper dentition within upper moldable material 24, the user or dental profession can better achieve the desired amount of mandibular advancement when upper tray 10 is engaged with a selected lower tray 40. In addition to centering the user's teeth within channel 25, V-shaped portion 26 and U-shaped portion 27 promote increased contact between the user's dentition and upper moldable material 24. Accordingly, an improved impression of the user's dentition is obtained during the fitting process.

FIGS. 7-10 are front, bottom, top, and side plan views, respectively, of lower tray 40 for oral appliance 1 of FIG. 1. Lower tray 40 is generally U-shaped (e.g., with two legs 46b, 46c extending from a vertex 46a). Lower tray 40 includes a lower support member 41 and a lower moldable material 54.

Figure 8:
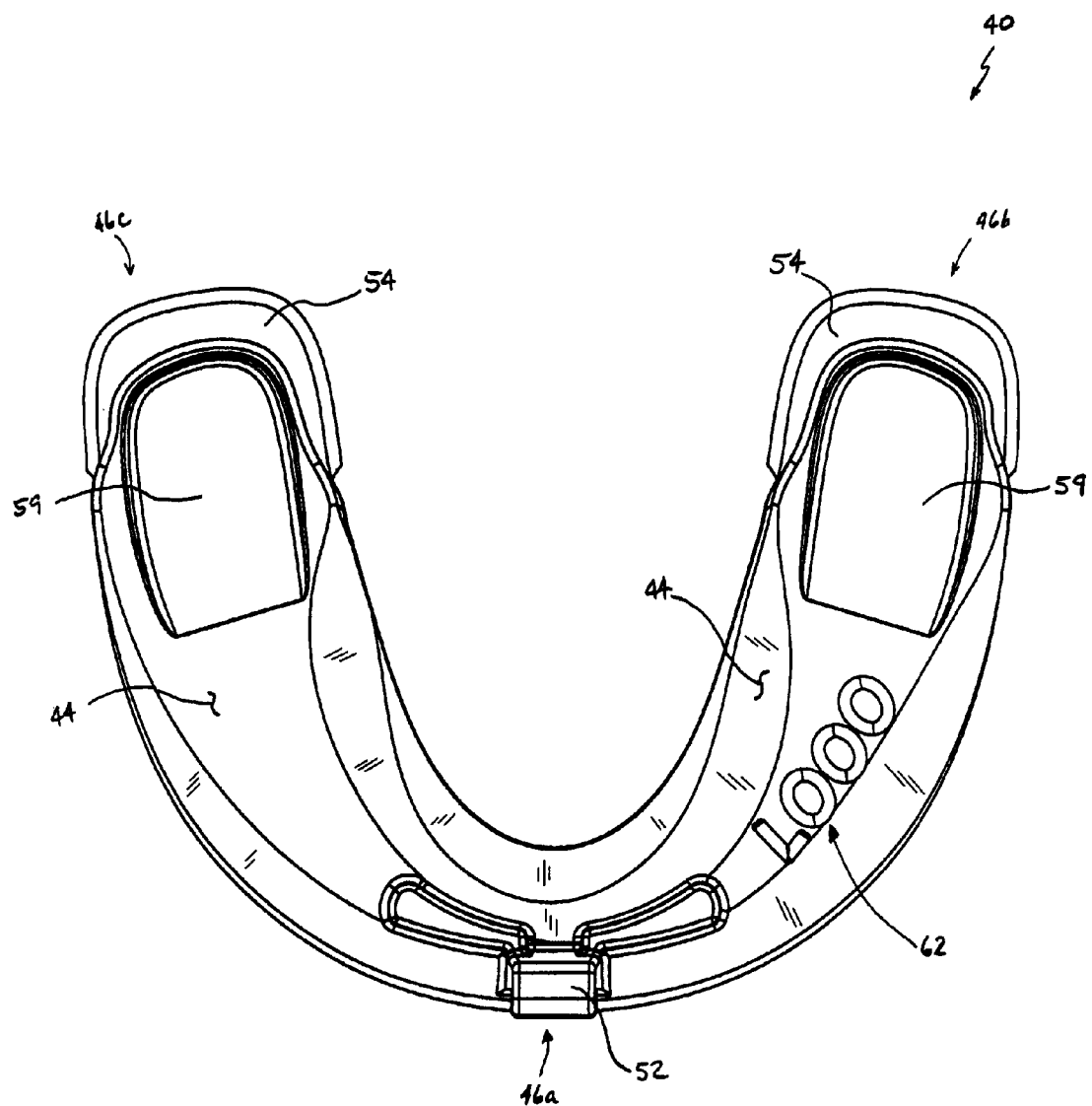
FIG. 8 is a bottom plan view of the lower tray illustrated in FIG. 7.
Figure 10:
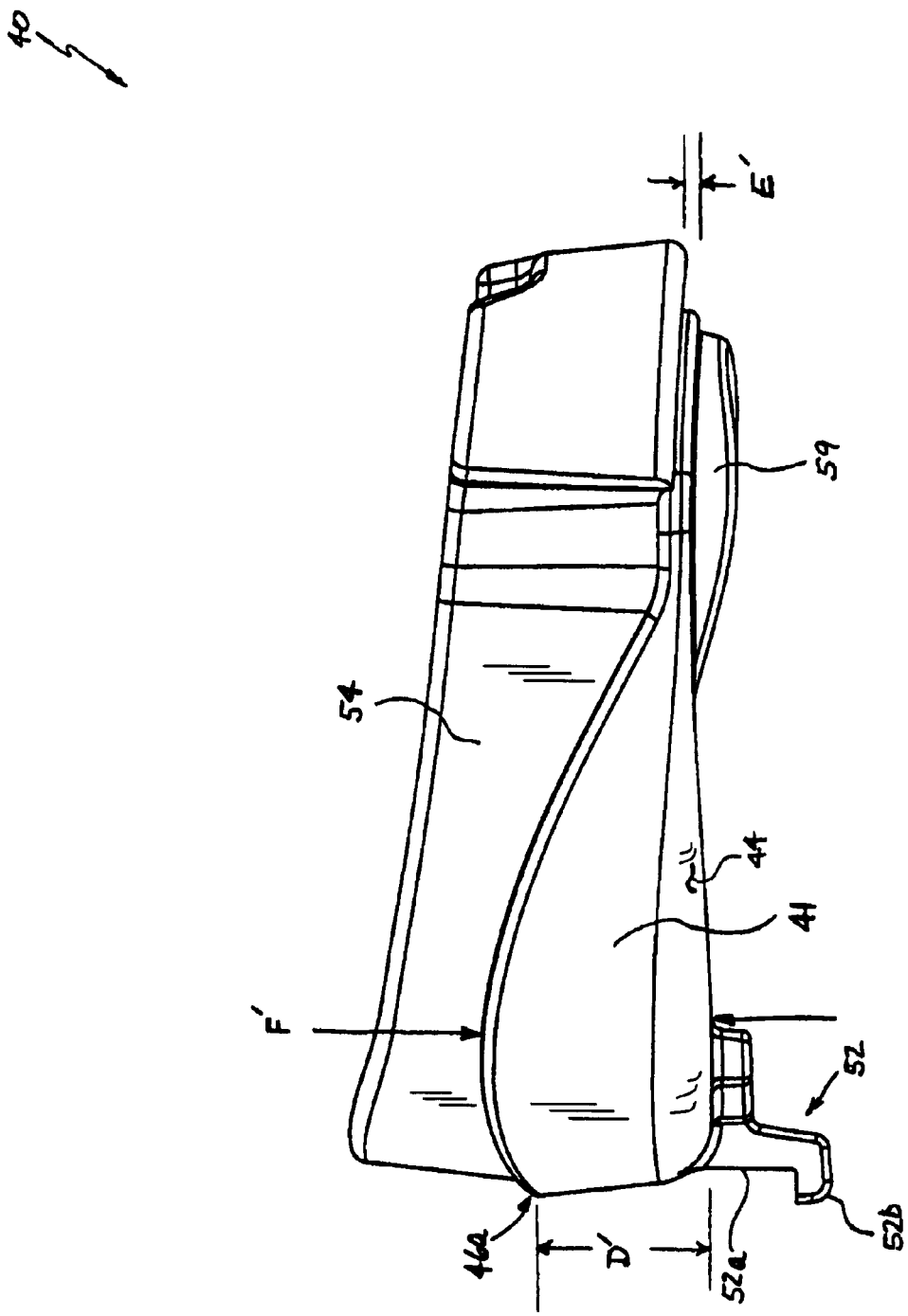
FIG. 10 is a side plan view of the lower tray illustrated in FIG. 7.
Figure 11:
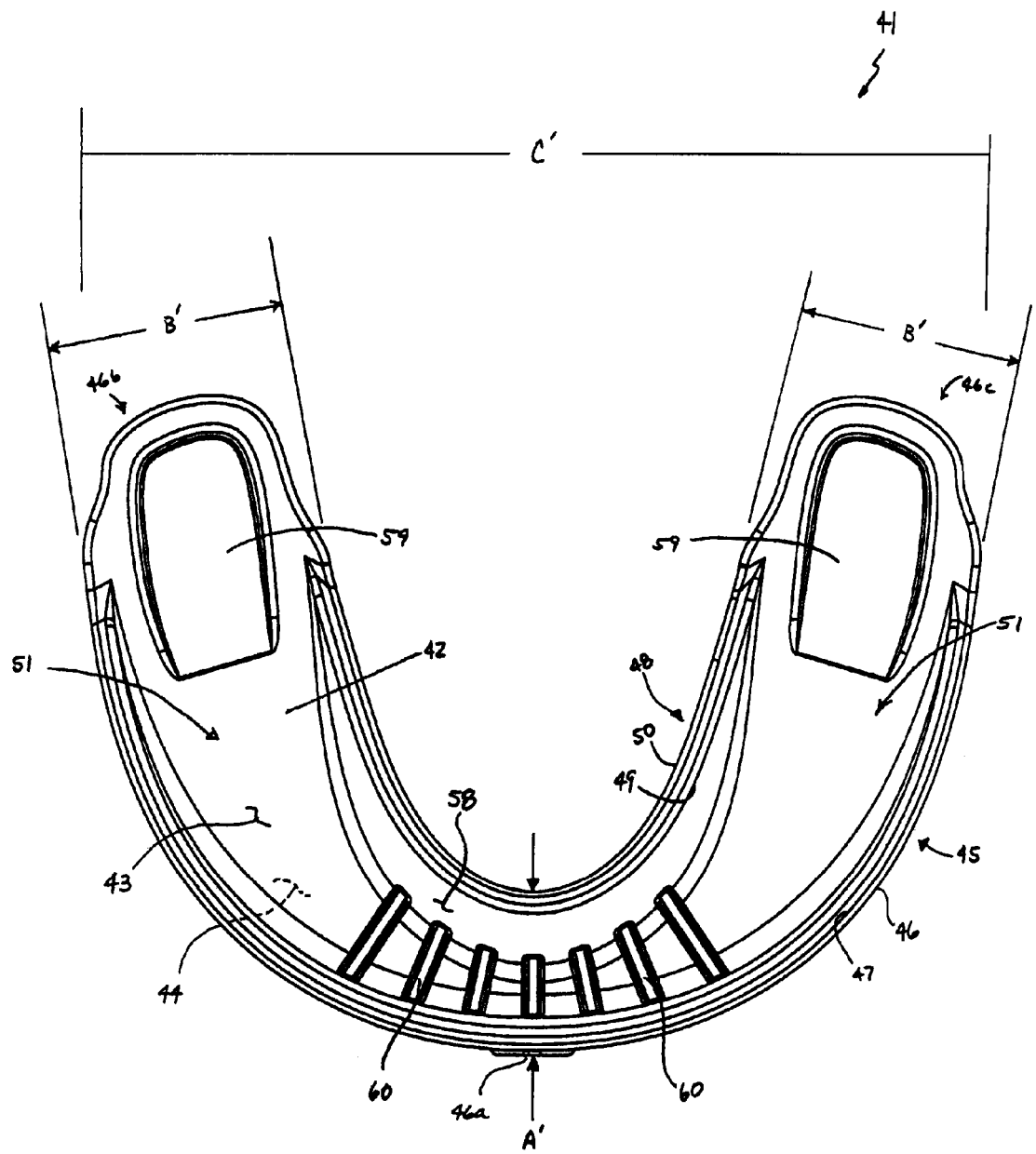
FIG. 11 is a top plan view of the lower support member portion of the lower tray illustrated in FIG. 7.

A top plan view of lower support member 41 without lower moldable material 54 coupled thereto, for one embodiment, is illustrated in FIG. 11. Lower support member 41 has a base 42 with a bonding surface 43 and an occlusal surface 44, an outer wall 45 with a front surface 46 and a rear surface 47, and an inner wall 48 with a front surface 49 and a rear surface 50. An elongated engagement member 52 (FIG. 10) extends from occlusal surface 44. A ramp 58 slopes downwardly from the top of a portion of inner wall 48 to a number of ribs 60 on bonding surface 43. As will be discussed in greater detail below, ramp 58 is structured to assist with centering the user's dentition relative to tray 40 during fitting while ribs 60 are structured to help provide the desired vertical spacing between the patient's maxillary and mandibular dentition. Lower support member 41 may include identification markings 62. In the current embodiment, for example and without limitation, lower support member 41 includes the letter "L" and the numeral "000" on occlusal surface 14 (FIG. 8).

Traveling from leg 46b to leg 46c along base 42, bonding surface 43 generally lies on a single plane (i.e., bonding surface 43 is generally flat). In an alternative embodiment, however, it is contemplated that bonding surface 43 may be somewhat curved in order to better accommodate the Curve of Spee associated with a user's dentition. Specifically, it is contemplated that bonding surface 43 is somewhat convex to accommodate the concave Curve of Spee associated with a user's mandibular dentition.

In the current embodiment, legs 46b, 46c of lower support member 41 also include a number of bite pads 59 which are structured to help provide the desired vertical spacing (e.g., 10 millimeters of vertical spacing). Bite pads 59 may be sized to promote the proper bite angle during fitting such that of the user's bite pressure is distributed across the entire occlusal surface 44 of base 42 during the fitting process. In the current embodiment, bite pads 59 are similarly sized, however, different sized bite pads 59 are within the scope of the present invention Generally, lower support member 41 has a first width (A') at vertex 46a that is between approximately 0.30 inches (7.62 millimeters) and approximately 0.53 inches (13.46 millimeters). Lower support member 41 also has, relative to at least one of first leg 46b and second leg 46c, a second width (B') that is between approximately 0.50 inches (12.70 millimeters) and approximately 0.73 inches (18.54 millimeters). The distance between the outer portion of first leg 46b and the outer portion of second leg 46c is a third width (C') that is between approximately 2.0 inches (50.8 millimeters) and approximately 2.80 inches (71.12 millimeters). In the current embodiment, first width (A') is approximately 0.41 inches (10.41 millimeters), second width (B') is approximately 0.60 inches (15.24 millimeters), and third width (C') is approximately 2.27 inches (57.66 millimeters).

In the current embodiment, lower support member 41 is sized such that the ratio between first width (A') and second width (B') is between approximately 0.60 and approximately 0.73 and the ratio between first width (A') and third width (C') is between approximately 0.17 and 0.19. In the current embodiment, for example, the ratio between first width (A') and second width (B') is approximately 0.68 and the ratio between first width (A') and third width (C') is approximately 0.18.

Referring briefly to FIG. 10, lower support member 41 has, relative to vertex 46a, a first height (D') that is between approximately 0.30 inches (7.62 millimeters) and 0.5 inches (12.70 millimeters), and has a second height (E') relative to at least one of a first leg 46b and a second leg 46c that is between approximately 0.025 inches (0.635 millimeters) and approximately 0.42 inches (10.67 millimeters). In the current embodiment, first height (D') and second height (E') are selected such that the ratio between first height (D') and second height (E') is between approximately 0.083 and approximately 0.125. Furthermore, lower support member 41 has a maximum height (F') that is between approximately 0.30 inches (7.62 millimeters) and 0.48 inches (12.19 millimeters).

In the current embodiment, first height (D') is approximately 0.32 inches (8.13 millimeters), second height (E') is approximately 0.032 inches (0.813 millimeters), the ratio between second height (E') and first height (D') is approximately 0.1, and maximum height (F') is approximately 0.42 inches (10.67 millimeters).

Lower support member 41 may be constructed of any suitable rigid or semi-rigid material. In the current embodiment, lower support member 41 has a density that is approximately between 0.040 lb/in3 and 0.050 lb/in$^3$, a volume that is between approximately 0.12 in$^3$ and 0.22 in$^3$ and a weight that is between approximately 0.0071 lbs and 0.0081 lbs. For example, lower support member 41 is constructed of a polycarbonate resin thermoplastic, such as LEXAN, having a density of approximately 0.045 lb/in$^3$, a volume of approximately 0.18 in$^3$, and a weight of approximately 0.0081 lbs.

As mentioned above, upper tray 10 includes a ramp 30 (see FIG. 6) that slopes downwardly from the top of a portion of inner wall 18 to a shelf 31 located on the bonding surface 13 of base 12 and lower tray 40 includes a ramp 58 (see FIG. 11) that slopes downwardly from the top of a portion of inner wall 48 to a number of ribs 60 located on the bonding surface 43 of base 42. Ramp 30 is structured to assist in centering the user's maxillary dentition relative to upper tray 10 and ramp 58 is structured to assist in centering the user's mandibular dentition relative to lower tray 40 during fitting. Shelf 31 and ribs 60 are structured to help provide the desired vertical spacing between the user maxillary and mandibular dentition.

Returning to FIG. 11, lower support member 41 defines a lower region 51. Lower region 51 is generally defined, for example and without limitation, by base bonding surface 43, outer wall rear surface 47, and inner wall front surface 49. Lower region 51 is adapted to carry a portion of lower moldable material 54 therein. Lower moldable material 54 may be coupled to lower support member 41 in any suitable manner, for example and without limitation, using an adhesive.

Lower moldable material 54 is not restricted within lower region 51. As seen for example in FIGS. 7, 8, and 10, at least a portion of moldable material 54 extends out of lower region 51. In the current embodiment, it is contemplated that a portion of lower moldable material 54 extends at least 0.00984 inches (0.25 millimeters) above outer wall rear surface 47, at least 0.0256 inches (0.65 millimeters) above inner wall front surface 49, and at least 0.00394 inches (0.1 millimeters) from the end of bonding surface 43 of base 42 (i.e., from the end of the legs 46b, 46c of lower support member 41). It should be noted that the amount that moldable material 54 extends out of any portion of lower region 51 may be varied while remaining within the scope of the present invention.

As discussed above in conjunction with upper moldable material 24, a lower moldable material 54 may be selected which yields when heated, thereby conforming to the user's dentition during fitting, and re-hardens when cooled, thereby retaining the shape of the user's dentition imparted during fitting (i.e., a "boil and bite" material). In the current embodiment, for example, lower moldable material 54 is an ethylene-vinyl acetate copolymer resin, such as ELVAX, having a density of approximately 0.035 lb/in$^3$, a volume of approximately 0.66 in$^3$, and a weight of approximately 0.0231 lbs.

Oral appliance 1 incorporating a lower tray 40 provides the same benefits over other oral appliances which have a lower tray comprised solely of a moldable material or comprised of a moldable material which is substantially completely contained within a support member as were discussed above in conjunction with upper tray 10. Accordingly, for these and other reasons, lower support member 41 provides increased patient comfort and allows lower tray 40 to fit a greater range of dental arch sizes.

Figure 9:
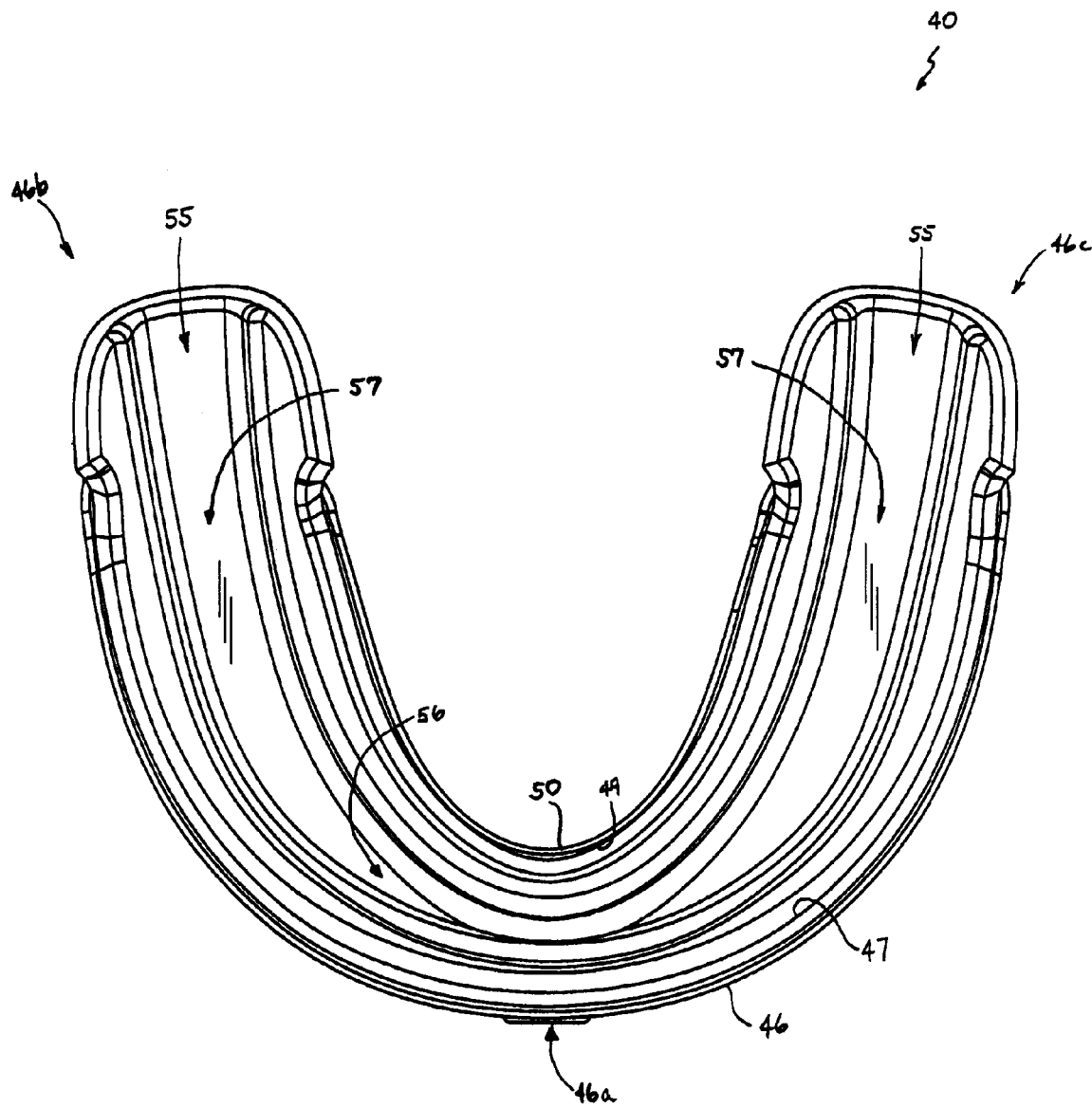
FIG. 9 is a top plan view of the lower tray illustrated in FIG. 7.

Referring now to FIG. 9, lower moldable material 54 has a channel 55 structured to center a user's dentition therein. More specifically, channel 55 includes a substantially V-shaped portion 56 structured to engage an anterior portion of the user's mandibular dentition (e.g., the lower centrals, laterals, and cuspids) and a substantially U-shaped portion 57 structured to engage a posterior portion of the user's mandibular dentition (e.g., the lower bicuspids and molars). By centering the user's lower dentition within lower moldable material 54, the user or dental profession can better achieve the desired amount of mandibular advancement when the selected lower tray 40 is engaged with upper tray 10. In addition to centering the user's teeth within channel 55, V-shaped portion 56 and U-shaped portion 57 promote increased contact between the user's dentition and lower moldable material 54. Accordingly, an improved impression of the user's dentition is obtained as a result of the fitting process.

Although the prior discussion of upper moldable material 24 and lower moldable material 54 was directed to the use of ELVAX, it should be noted that other materials and/or combinations of materials may be employed. For example, it is contemplated that upper moldable material 24 and/or lower moldable material 54 are comprised of a polycaprolactone polymer or other aliphatic polyester (for example and without limitation, TONE P-700, TONE P-767 or TONE P-787 polycaprolactone polymers manufactured by Union Carbide Corporation). U.S. Pat. Nos. 6,247,926 and 5,807,100, incorporated herein by reference, provides examples of the use of such materials.

As another example, it is contemplated that upper moldable material 24 and/or lower moldable material 54 are comprised of a combination of ELVAX and a polycaprolactone polymer or other aliphatic polyester Both the ELVAX and the polycaprolactone yield when heated. Accordingly, these materials are better able to flow around the user's dentition during the fitting process thereby providing a custom fit. After cooling, the ELVAX remains relatively flexible and promotes retention of the oral appliance 1 within the patient's mouth. The polycaprolactone, however, becomes relatively rigid after cooling. Accordingly, the polycaprolactone provides additional support to the ELVAX; support that may be lacking when the ELVAX is used alone. U.S. Pat. No. 5,051,476, incorporated herein by reference, provides one such example of the use of ELVAX and polycaprolactone.

Figure 20:
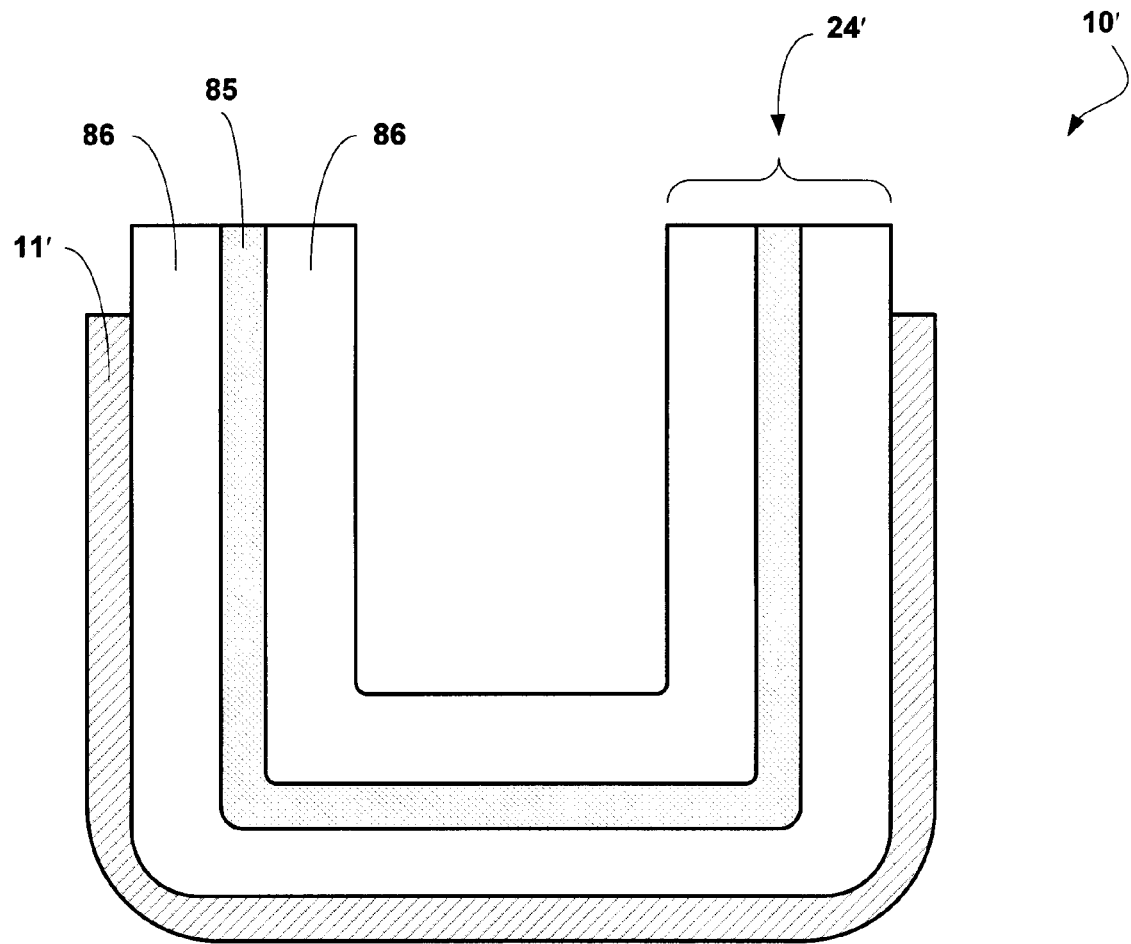
FIG. 20 illustrates a layered moldable material according to one embodiment of the present invention.
Figure 21:
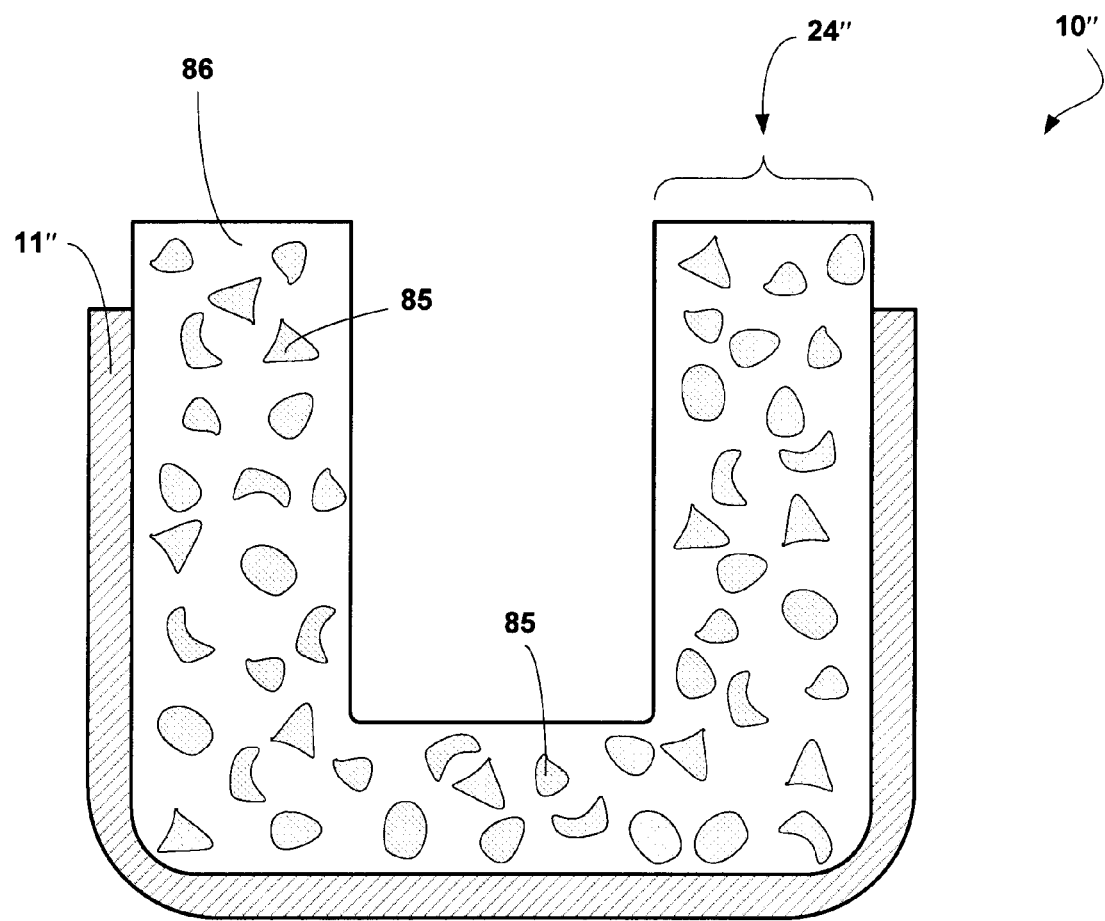
FIG. 21 illustrates an embedded molded material according to one embodiment of the present invention.

The specific arrangement of the ELVAX and polycaprolactone may be varied while remaining within the scope of the present invention. FIGS. 20-21, for instance, show cross sectional views of upper trays 10', 10" according to embodiments in which the moldable material 24', 24" includes a combination of ELVAX 86 and polycaprolactone 85. Referring to FIG. 20, ELVAX 86 and polycaprolactone 85 are arranged in alternating layers. Specifically, moldable material 24' includes a layer of polycaprolactone 85 sandwiched between two layers of ELVAX 86. As shown in FIG. 20, moldable material 24' is carried by support member 11', which in this instance, is constructed of polycarbonate. The present invention also contemplates eliminating one or more layers, for example and without limitation, eliminating the layer of ELVAX adjacent to support member 11'. Referring to FIG. 21, polycaprolactone 85 is suspended within and throughout ELVAX 86. Moldable material 24" is carried by support member 11", which in this instance, is also constructed of polycarbonate.

Figure 12:
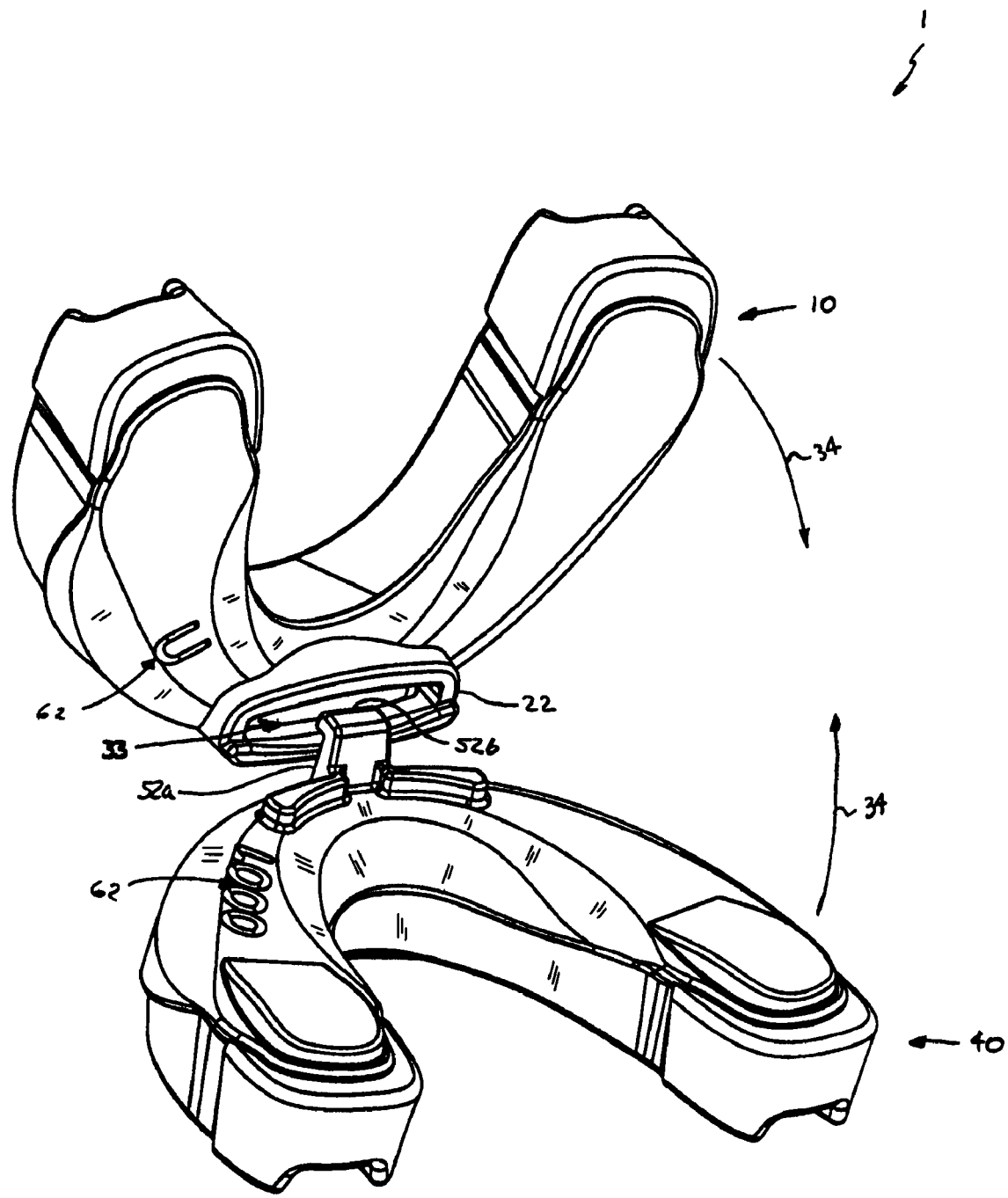
FIG. 12 illustrates the engagement of the upper and lower trays according to one embodiment.

FIG. 12 illustrates the engagement of upper tray 10 and lower tray 40. Typically, lower tray 40 is arranged approximately perpendicular to upper tray 10. A leading edge 52a of elongated engagement member 52 is brought into contact with a portion of slotted engagement member 22 such that end 52b is inserted into a bottom slot 33 of slotted engagement member 22. Lower tray 40 and upper tray 10 are then rotated, relative to each other, as indicated by directional arrows 34, such that end 52b enters front slot 32 (see FIG. 1) and is "hooked". When engaged, as seen in FIG. 1, end 52b, is capable of moving a predetermined amount laterally (as indicated by directional arrow 35) and a predetermined amount vertically (as indicated by directional arrow 36) within slotted engagement member 22. In the current embodiment, for instance, end 52b can move between 10-13 millimeters laterally and between 0.8-1.2 millimeters vertically. It should be noted, however, that the amount of predetermined lateral and vertical movement may be altered while remaining within the scope of the present invention.

Although the engagement of upper tray 10 with lower tray 40 are described in conjunction with slotted engagement member 22 and elongated engagement member 52 (i.e., a hook and slot arrangement), alternative engagement mechanisms may be employed while remaining within the scope of the present invention. Furthermore, the specific arrangement of the engagement members may be altered while remaining within the scope of the present invention. For example, slotted engagement member 22 may extend from lower support member 41 of lower tray 40 and the elongated support member 52 may extend from upper support member 11. As further examples, and without limitation, the length of elongated engagement member 52, the size of hook end 52*b*, and the orientation of hook end 52*b* may be altered while remaining within the scope of the present invention.

In the current embodiment, slotted engagement member 22 includes a frangible portion 23 (see FIG. 2) which is structured to break when approximately 36 lbs of force are applied thereto. Frangible portion 23, however, may be structured to break when a different amount of predetermined amount of force is applied thereto. Furthermore, the applied force at which frangible portion 23 breaks may vary depending upon the direction that the force is applied. Additionally, or alternatively, elongated engagement member 52 may include a frangible portion (not shown).

As discussed above, each of the multiple lower trays 40 is structured to impart a different fixed amount of mandibular advancement when engaged with upper tray 10. In the current embodiment, the amount of mandibular advancement imparted by each lower tray 40 is determined by the fixed placement of elongated engagement member 52 relative to, for example, vertex 46*a* of the outer wall front surface 46 at vertex 46*a*.

For lower tray 40 illustrated in FIGS. 7-10, for example, leading edge 52*a* of elongated engagement member 52 is offset approximately 1.70 millimeters from the outer wall front surface at vertex 46*a* of the outer wall front surface 46. At this position, lower tray 40 is structured to provide a fixed amount of mandibular advancement which brings the user's lower central teeth into alignment with the user's upper central teeth in the current embodiment.

Figure 13:
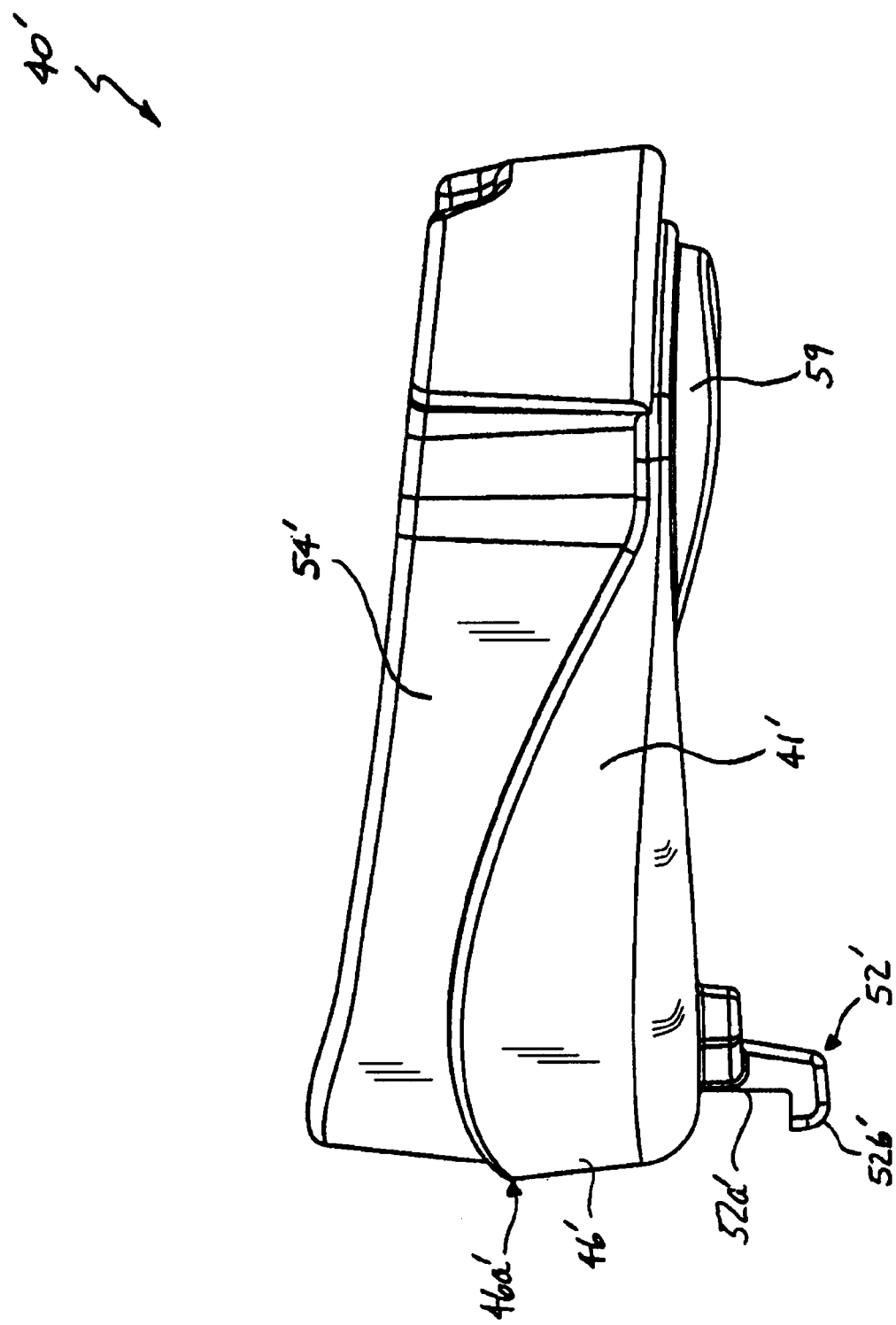
FIG. 13 is a side plan view of a lower tray for the oral appliance illustrated in FIG. 1 according to another embodiment.

Lower tray 40' illustrated in FIG. 13, as another example, is structured to provide a fixed amount of mandibular advancement such that the user's lower central teeth extend approximately 0.098 inches (2.5 millimeters) out from the user's upper central teeth (i.e., lower tray 40' imparts a Class III malocclusion or "underbite"). Specifically, leading edge 52*a'* of elongated engagement member 52' is offset approximately 4.20 millimeters relative to the outer wall front surface 46' at vertex 46*a'*. Although the current discussion was limited to lower tray 40 and lower tray 40', it is contemplated that other lower trays which impart different fixed amounts of mandibular advancement may be provided. For example, it is contemplated that oral appliance 1 also includes an additional lower tray which provides fixed mandibular advancement such that the user's lower central teeth extend approximately 0.197 inches (5 millimeters) out from the user's upper central teeth.

Because upper tray 10 and lower tray 40 are asymmetric, the amount of mandibular advancement may also be varied by flipping upper tray 10 and lower tray 40. For example, when upper tray 10 is fitted to a user's maxillary dentition and lower tray 40 is fitted to the user's mandibular dentition; oral appliance 1 imparts an amount of mandibular advancement to cause the user's upper central teeth to be aligned with the user's lower central teeth. However, if upper tray 10 is fitted to the user's mandibular dentition and lower tray 40 is fitted to the user's maxillary dentition; oral appliance 1 imparts an amount of mandibular advancement to cause the user's lower central teeth to extend approximately 0.197 inches (5 millimeters) out from the user's central upper teeth (i.e., to cause a Class III malocclusion or "underbite"). Accordingly, a small number of lower trays may be needed to obtain a larger range of mandibular advancement.

Figure 14:
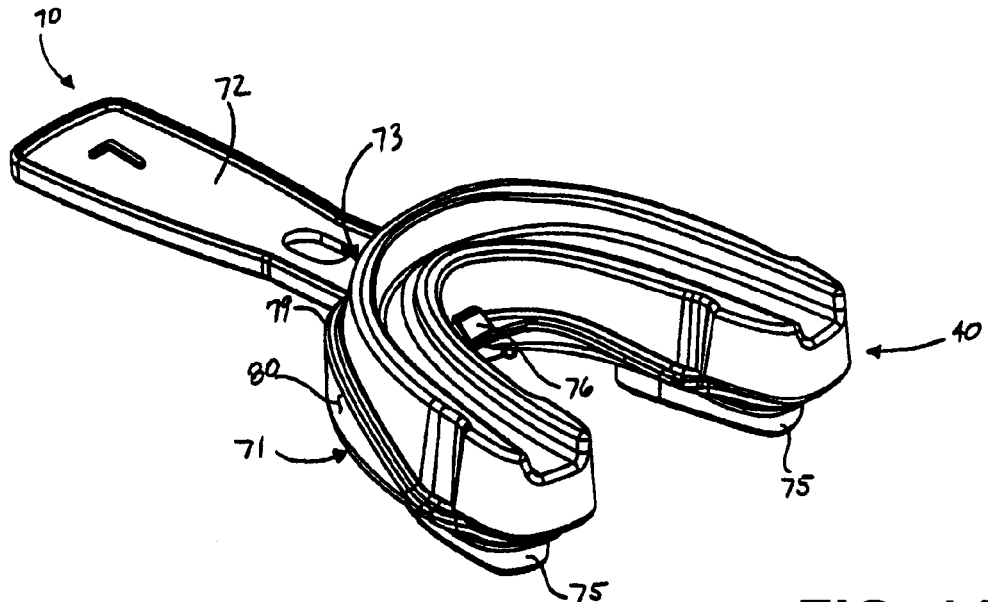
FIG. 14 is top perspective view of a holding tray engaged with a lower tray according to one embodiment.
Figure 15:
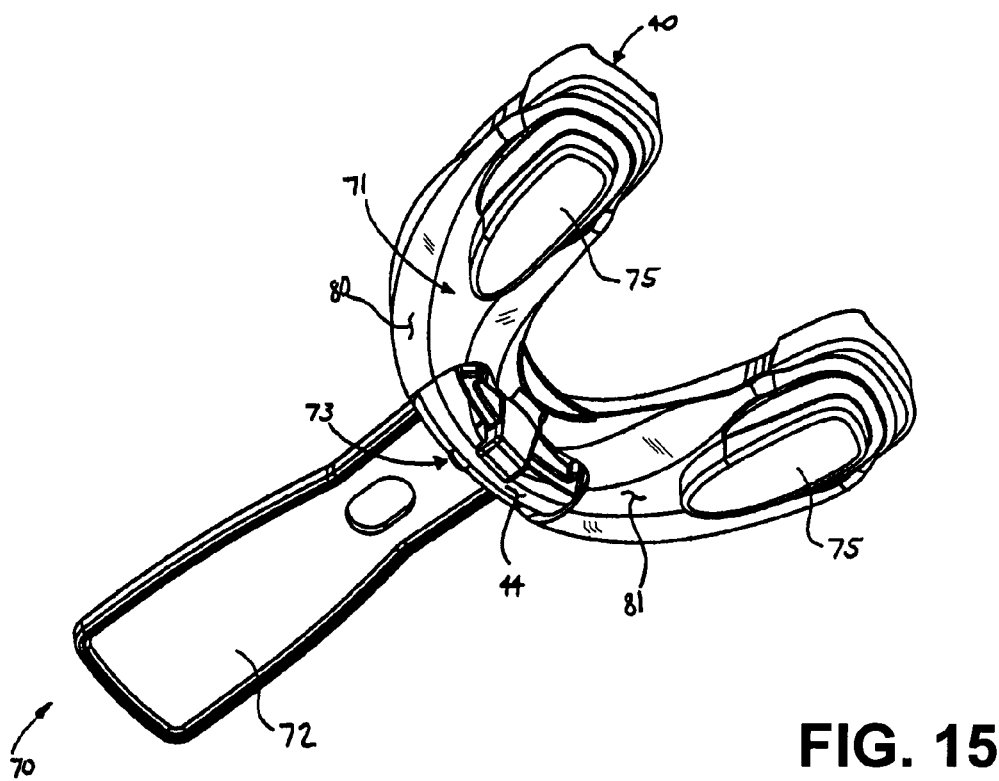
FIG. 15 is bottom perspective view of the holding tray and lower tray of FIG. 14.
Figure 16:
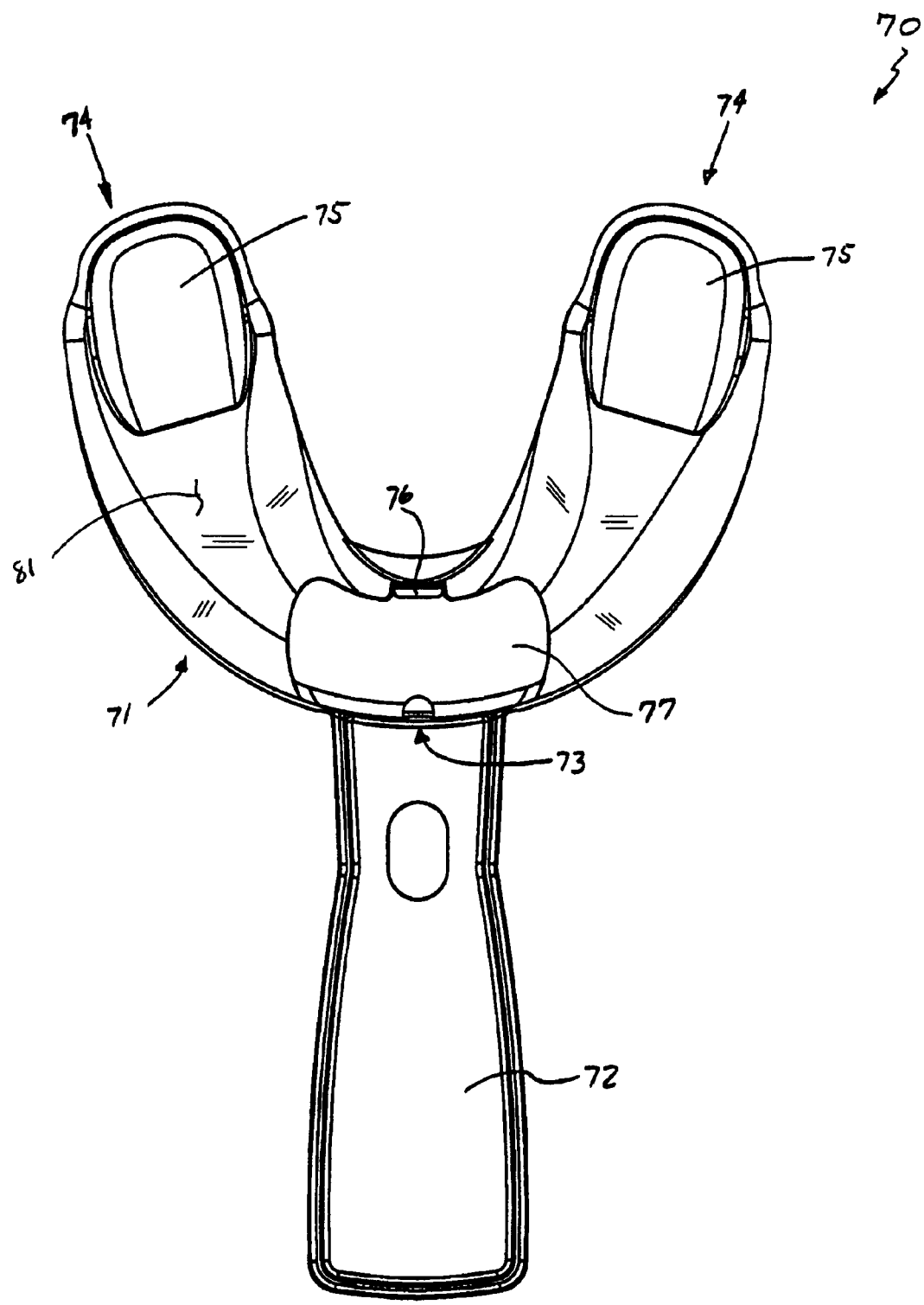
FIG. 16 is a bottom plan view of the holding tray illustrated in FIG. 14 according to one embodiment.

Oral appliance 1 may be part of an assembly/system which includes a number of holding trays which are structured to couple with the upper and lower trays. FIGS. 14 and 15, for example, illustrate a holding tray 70 engaged with lower tray 40 and FIG. 16 is a bottom plan view of holding tray 70 according to one embodiment. Holding tray 70 includes a generally U-shaped frame 71 which is sized to accept lower tray 40 therein. Frame 71 includes a base 78 with an outer wall 79 extending therefrom.

In the current embodiment, base 78 includes a gate 77 which is structured to accommodate elongated engagement member 52. An ejector pin 76 is employed to maintain lower tray 40 in contact with holding tray 70. In the current embodiment, ejector pin 76 is located along the posterior side of gate 77. Accordingly, when lower tray 40 and holding tray 70 are coupled, ejector pin 76 engages inner wall 48 such that lower tray 40 "snaps-into" holding tray 70.

In the current embodiment, holding tray 70 also includes a handle 72 which projects from a front surface 80 of outer wall 79 at vertex 73 of frame 71. Handle 70 may be employed by the user to suspend lower tray 40 within a heating medium during the fitting process. For "boil and bite" moldable materials, for example, a user may grasp and hold handle 72 while moldable material 54 is submerged within the boiling water. Once moldable material 54 has yielded (e.g., has become soft enough to be reshaped or molded), the user may remove lower tray 40 from the boiling water and insert lower tray 40 into their mouth. Holding tray 70 promotes proper insertion of lower tray 40 into a user's mouth during the fitting process. Specifically, a user employing holding tray 70 has the additional leverage provided by handle 72 to better align lower tray 40 within their mouth.

An occlusal surface 81 of base 78 may include a number of bite pads 75 located thereon. Bite pads 75 may be constructed of an elastomeric material that increases the user's comfort during the fitting process although other materials are contemplated. Additionally, bite pads 75 may be sized to promote the proper bite angle during fitting such that of the user's bite pressure is distributed across the entire occlusal surface 81 of base 78 during the fitting process. In the current embodiment, bite pads 75 are similarly sized, however, different sized bite pads 75 are within the scope of the present invention.

It should be apparent that modifications may be made to holding tray 70 while remaining within the scope of the present invention. For example and without limitation, holding tray 70 may have an ejector pin 76 located along the anterior side of gate 77 and an inner wall which engages outer wall 45 such that lower tray 40 "snaps-into" holding tray 70. Although the discussion associated with FIGS. 14-16 was generally limited to using holding tray 70 in conjunction with lower tray 40, it should be apparent that holding tray 70 may also be structured for use with other lower trays and/or upper tray 10.

Figure 17:
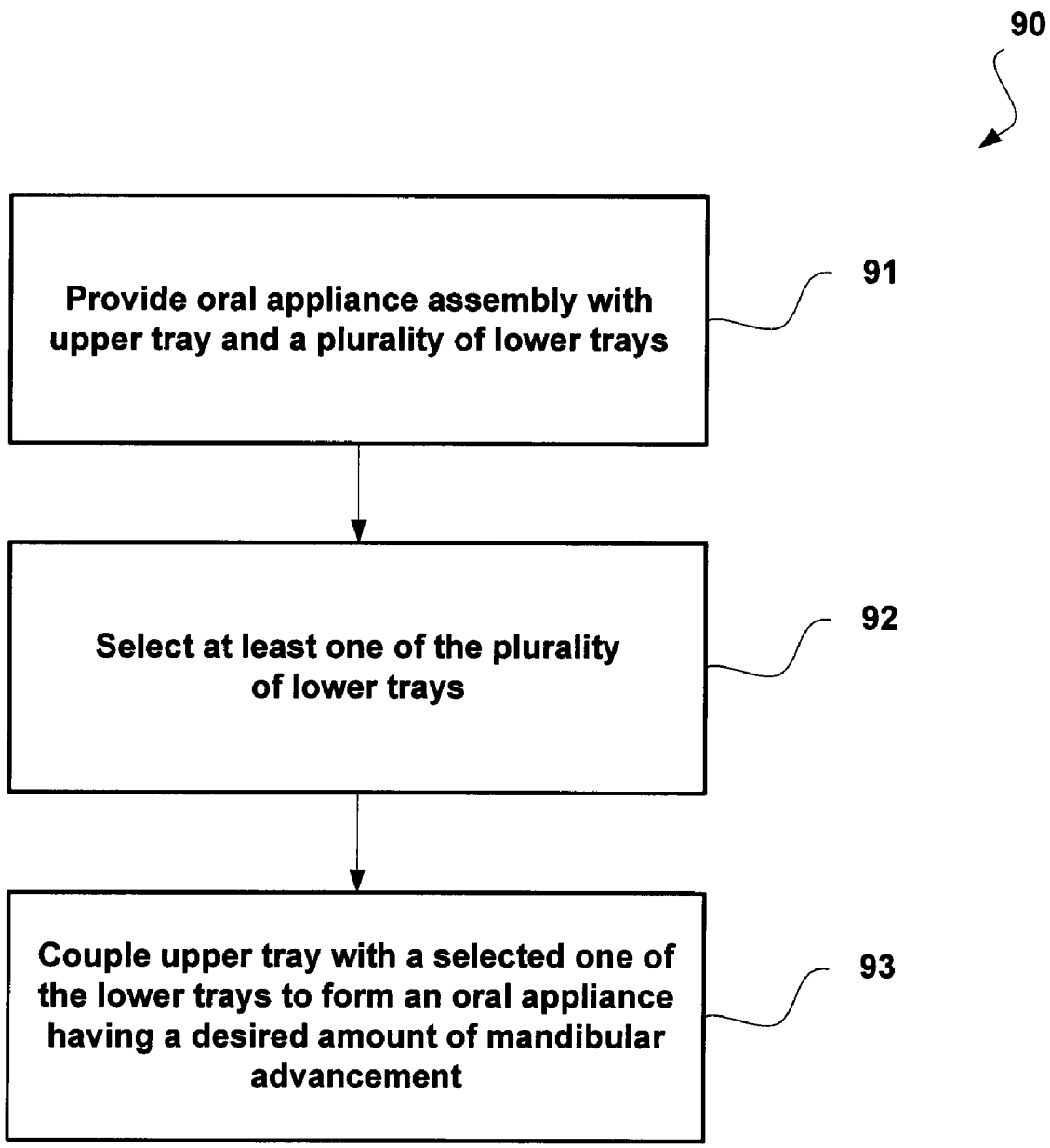
FIG. 17 illustrates an operational process for effecting the patency of a user's airway according to one embodiment.

FIG. 17 illustrates operational process 90 for effecting the patency of a user's airway according to one embodiment. Operational process begins at operation 91 which provides an oral appliance assembly including an oral appliance, such as oral appliance 1 shown in FIG. 1, having an upper tray and plurality of lower trays. In the current embodiment, upper tray 10 is adaptable to conform to a user's maxillary dentition and each of the plurality of lower trays 40, 40' is adaptable to conform to the user's mandibular dentition. Upper tray 10 and lower tray(s) 40, 40' may be fitted to a user's maxillary dentition and mandibular dentition, respectively, using for example, operational process 100 and operational process 110 which will be described in more detail below. Each of at least some of lower trays 40, 40' is structured to couple with upper tray 10 to impart a different fixed amount of mandibular advancement.

Operational control is passed to operation 92 after the oral appliance assembly is provided in operation 91. At Operation 92, at least one of the plurality of lower trays is selected. In the current embodiment, a lower tray may be selected based upon the particular amount of mandibular advancement that is desired. For example and without limitation, lower tray 40 is structured to provide a fixed amount of mandibular advancement to bring the user's lower central teeth into alignment with the user's upper central teeth, whereas lower tray 40' is structured to provide a fixed amount of mandibular advancement such that the user's lower central teeth extend approximately 2.5 millimeters out from the user's upper central teeth (i.e., lower tray 40' imparts a Class III malocclusion or "underbite"). The selection of the proper lower tray may be made by a dental professional, a user, or others.

Operational control is passed to operation 93 after one of the lower trays is selected. At Operation 93, the upper tray is coupled with the selected lower tray to form an oral appliance having a desired amount of mandibular advancement. In the current embodiment, upper tray 10 includes a slotted engagement member 22 and lower trays 40, 40' include an elongated engagement member 52. Upper tray 10 and selected lower tray 40, 40' may be coupled as described above in conjunction with FIG. 12. After the upper and lower trays are coupled, oral appliance may be inserted into the user's mouth to effect the patency of a user's airway.

Figure 18:
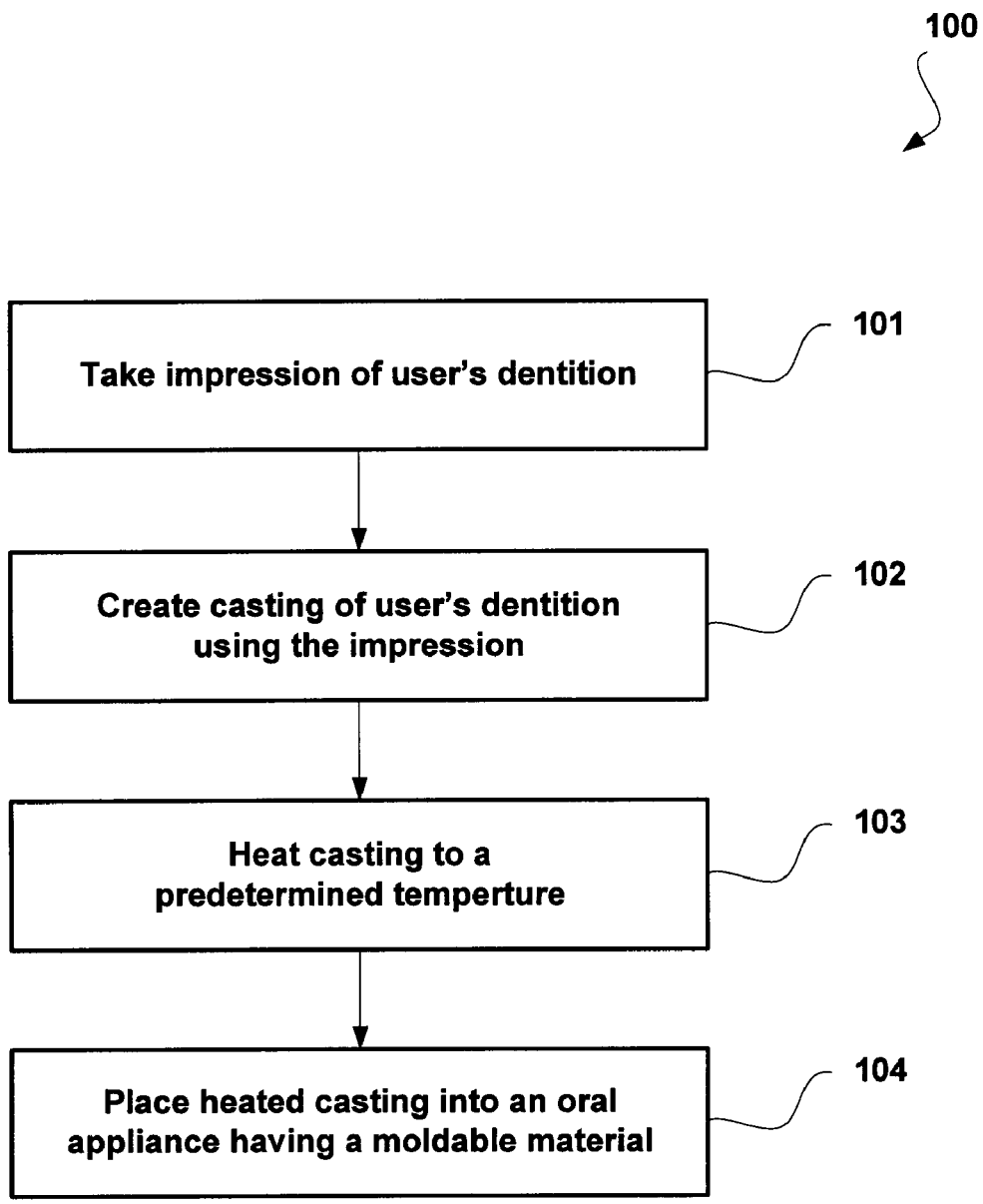
FIG. 18 illustrates an operational process for fitting an oral appliance according to one embodiment.

FIG. 18 illustrates operational process 100 for fitting an oral appliance according to one embodiment. Operational process 100 begins with taking an imprint of a user's dentition at operation 101. An imprint is generally a negative likeness of the user's dentition. Typically, the imprint is taken by a dental professional using a plastic material which hardens or sets while in contact with the user's dentition. In the current embodiment, two imprints are taken: the first is an imprint of the user's maxillary dentition and the second is an imprint of the user's mandibular dentition.

After the imprint is completed, operational control is passed to operation 102 at which a casting of the user's dentition is created. The casting may be made, for example, by filling the imprint with plaster of Paris or artificial stone. In the current embodiment, castings of both the user's maxillary and mandibular dentition are created. Once completed, the castings provide a facsimile of the user's maxillary and mandibular dentition.

The casting is then heated to a predetermined temperature at operation 103. In the current embodiment, each casting created at operation 102 is placed in heating medium, for example and without limitation, water. The temperature of the heating medium is maintained between approximately 180° and 220° Fahrenheit (between approximately 82.22° and 104.4° Celsius). In addition, in the current embodiment, top tray 10 and a selected lower tray 40 are also placed in the heating medium such that moldable material 24 and moldable material 54 begin to yield (i.e., soften). It should be noted that the manner of heating and the value of the predetermined temperature may be altered while remaining within the scope of the present invention.

After reaching the predetermined temperature, the casting is pressed into the moldable material of an oral appliance. In the current embodiment, the heated casting of the user's maxillary dentition is placed within upper moldable material 24 of upper tray 10. The heat retained by this casting permits upper moldable material 24 to remain in a yielded state for a longer period of time, thereby allowing a more accurate impression of the user's maxillary dentition to be formed within upper moldable material 24. Once cooled, upper moldable material 24 has been fit to the user's maxillary dentition. Likewise, the heated casting of the user's mandibular dentition is placed within lower moldable material 54 of lower tray 40. The heat retained by this casting permits lower moldable material 54 to remain in a yielded state for a longer period of time, thereby allowing a more accurate impression of the user's mandibular dentition to be formed within lower moldable material 54. Once cooled, lower moldable material 54 has been fit to the user's mandibular dentition.

Figure 19:
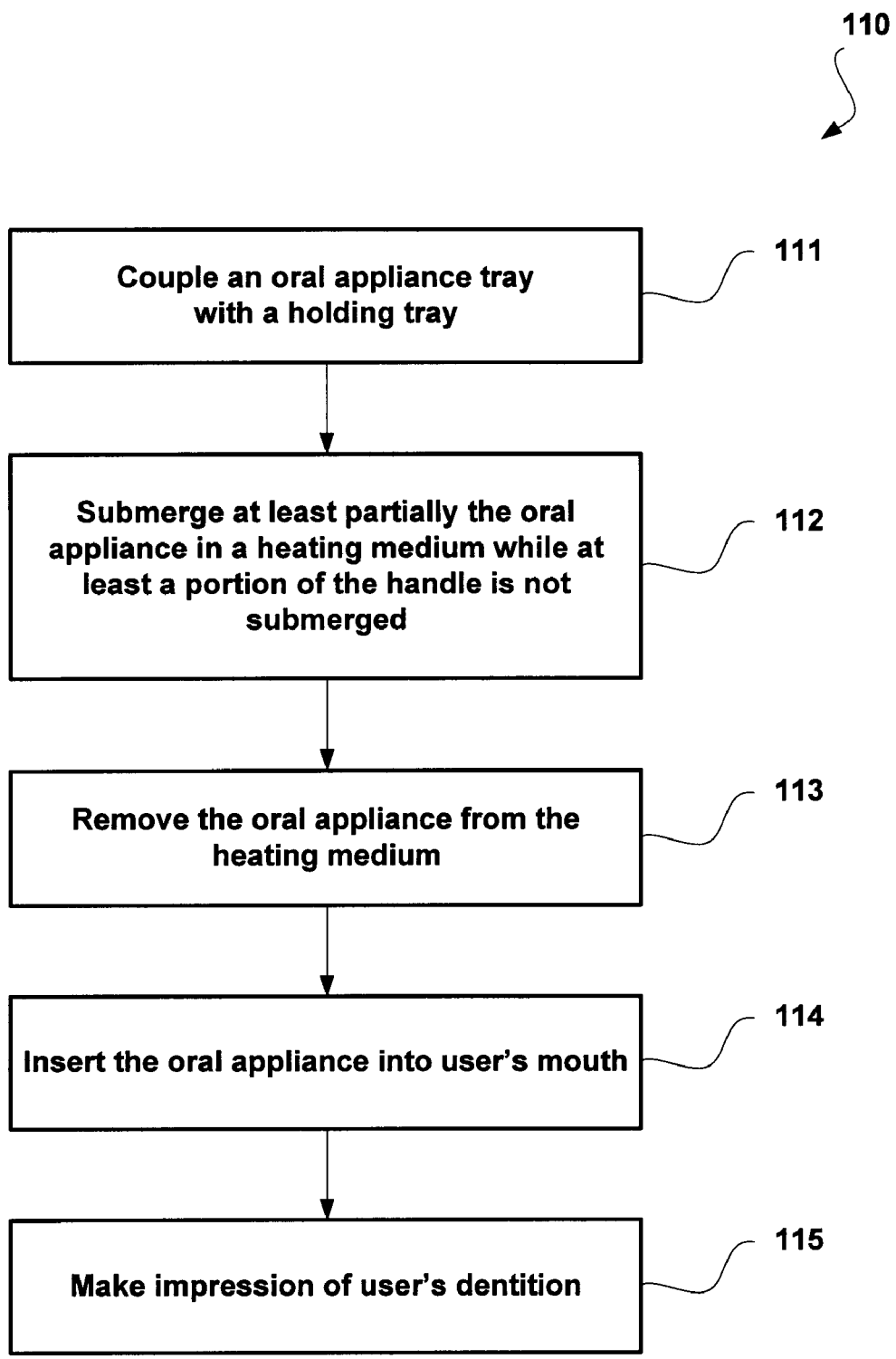
FIG. 19 illustrates operational process for fitting an oral appliance according to another embodiment.

FIG. 19 illustrates operational process 110 for fitting an oral appliance according to another embodiment. Operational process 110 begins when an oral appliance tray is coupled with a holding tray at operation 111. In the current embodiment, the oral appliance tray is at least one of an upper tray 10 with moldable material 24 and a lower tray 40, 40' with moldable material 54, 54' and holding tray 70 has a handle 72 attached thereto.

After the oral appliance tray and the holding tray are coupled, operational control is passed to operation 112 at which the oral appliance tray is submerged within a heating medium while at least a least a portion of the handle remains out of the heating medium. With reference to an upper tray 10, for example, a user can grasp an end of handle 72 and submerge upper tray 10 within boiling water. The user may continue to hold handle 72 (which is not submerged in the boiling water) while upper tray 10 is submerged.

Operational control is then passed to operation 113 at which the oral appliance tray is removed from the heating medium with the handle. Continuing the example above, a user can remove upper tray 10 from the boiling water (with handle 72) after upper moldable material 24 reaches a yielded state.

Operational control is then passed to operation 114 at which the oral appliance tray is inserted into a user's mouth using the handle. Continuing with the same example, a user can insert upper tray 10 into their mouth while maintaining a grip on handle 72. Handle 72 provides additional leverage to the user such that proper alignment of upper tray 72 within the user's mouth is facilitated. Additionally, handle 72 eliminates the need for the user to touch upper tray 10 which may still be somewhat hot from being submerged within the boiling water.

After the oral appliance tray is inserted into the user's mouth, operational control is passed to operation 115 at which an impression of at least a portion of the user's dentition is made. In the current example, the user is able to bite into upper moldable material 24 which is in a yielded state. Upper moldable material 24 then flows around the user's dentition to form the impression.

Although both operational process 100 and operational process 110 can be used for fitting oral appliance 1, operational process 100 may provide more accurate results than operational process 110. Generally, a casting retains more heat than the moldable material. This heat is transferred from the casting to the moldable material, thus causing the moldable material to remain in the yielded state for an increase length of time as compared to heating the moldable material alone (e.g., operational process 110). Because the moldable material is in the yielded state for a longer length of time, the moldable material has a better opportunity to flow around the casting and form the impression. Furthermore, once placed in the moldable material, the casting remains substantially stationary; whereas a user biting directly into the moldable material (operational process 110) will move his/her jaw.

Oral appliance 1 also may be adapted for use with a patient interface device. A patient receiving treatment for sleep apnea, for instance, may be required to wear a nasal mask, oral mask, full-face mask, or other patient interface device. Examples of oral appliances used in combination with a patient interface device are found in U.S. Pat. Nos. 2,521,084;

4,470,413; 5,573,994; 5,752,510; 5,954,048; 6,012,455; 6,405,729; 6,789,543; and 7,021,312. The content of each of these patents is incorporated herein by reference.

Figure 22:
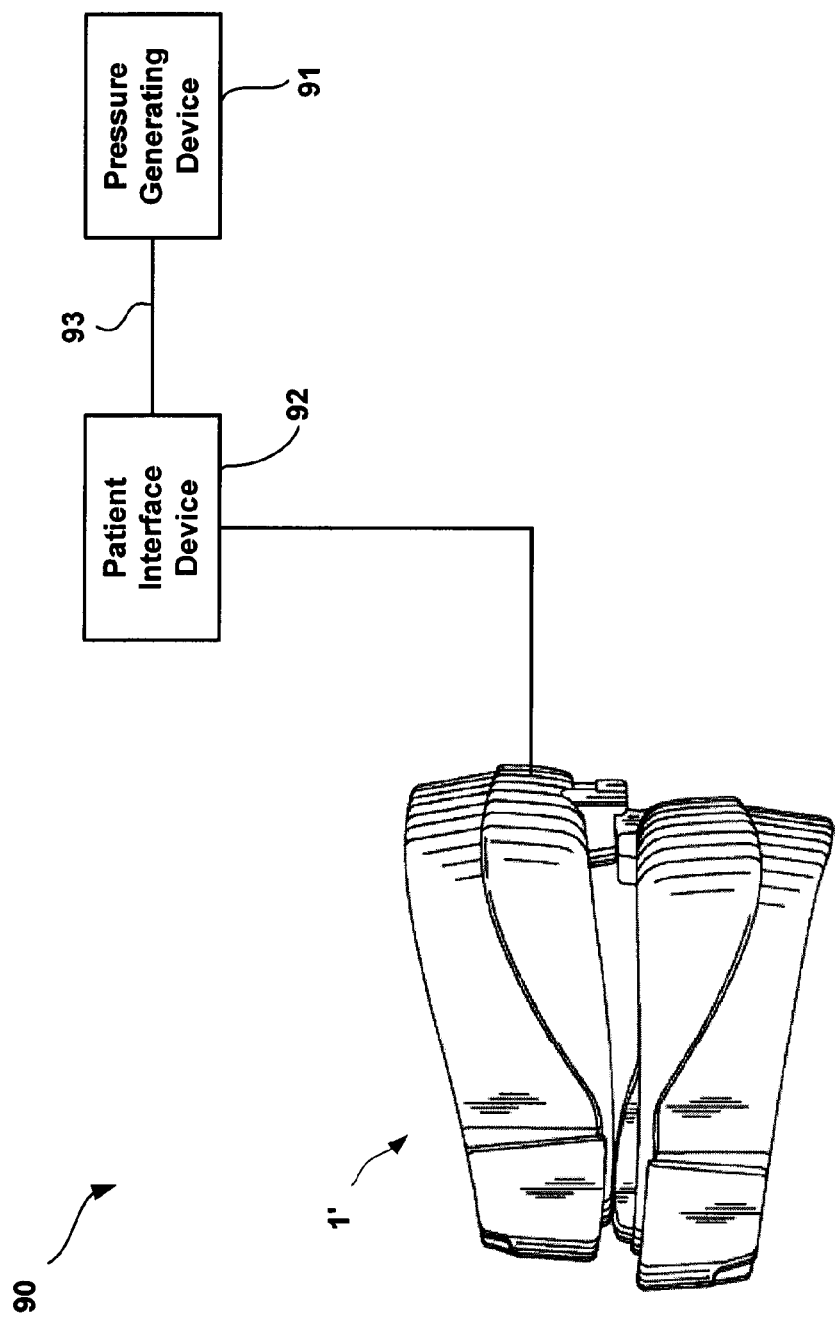
FIG. 22 illustrates the oral appliance of FIG. 1 schematically coupled with a patient interface device.

FIG. 22 illustrates a system 90 for treating sleep apnea and/or other respiratory ailments. In the current embodiment, system 90 includes a pressure generating device 91, a nasal mask 92, a conduit 93, and oral appliance 1'. Oral appliance 1' is shown schematically coupled with nasal mask 92 which is operatively connected to pressure generating device 91 via conduit 93. Oral appliance 1' is structured to stabilize nasal mask 92 relative to the patient's face. Nasal mask 92 is structured to deliver, to the patient's airway, a flow of pressurized breathing gas produced by gas generating device 91. By coupling with oral appliance 1', nasal appliance 92 is better secured to the patient's face and the patient's sleep apnea and/or other respiratory aliments are treated through both mandibular advancement and the application of positive airway pressure. It is contemplated that oral appliance 1' may be coupled with the patient interface device in any suitable manner.

Figure 23:
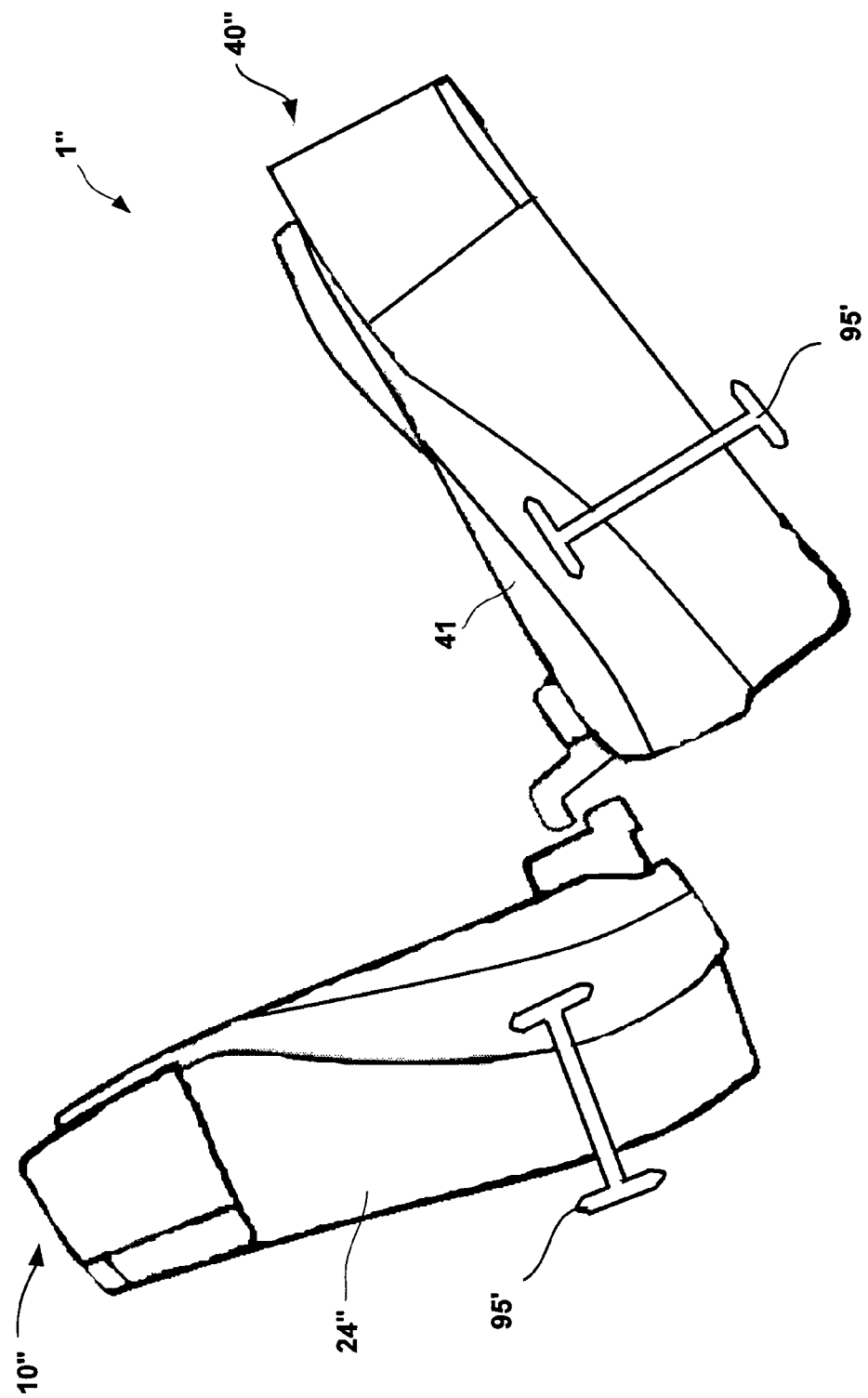
FIG. 23 illustrates the oral appliance of FIG. 1 with electromyography electrodes according to one embodiment.

Oral appliance 1 may also be adapted to be used in combination with a patient monitoring device and/or intraoral electromuscular stimulation device. Examples of oral appliances with electrodes extending therefrom for use with a patient monitoring device and/or intraoral electromuscular stimulation device are found in U.S. Pat. Nos. 6,618,627 and 5,190,053. The content of each of these patents is incorporated herein by reference. FIG. 23 illustrates oral appliance 1" with electrodes 95, 95' extending therefrom according to one embodiment.

Electrodes 95, 95' may be structured, for example, to capture electromyography (EMG) activity produced by one or more of the patient's muscles (e.g., the masseter muscle). Measured EMG activity may be employed, for example and without limitation, to monitor bruxism and oral appliance wear compliance. EMG electrodes 95, 95' may be placed at any suitable location on oral appliance 1" such that, after fitting oral appliance 1", the EMG activity of the targeted muscle may be captured. As shown in FIG. 23, for example, EMG electrodes 95 are placed in upper moldable material 24", and EMG electrodes 95' are placed on lower support member 41". A monitoring system (not shown) wirelessly communicates with EMG electrodes 95, 95'. The monitoring system may include a processor for analyzing the EMG activity detected in the masseter muscle.

Electrodes 95, 95' may be structured, as another example, to provide intraoral electromuscular stimulation to reduce or minimize the occurrence of a breathing disorder, such as obstructive sleep apnea. Intraoral electromuscular stimulation may be employed, for instance, to provide electrical stimulation to the muscles of the upper airway responsible for maintaining the patency of the airway. Generally, electromuscular stimulation induces contraction in the muscles of the upper airway, thereby preventing or minimizing blockage of a user's airway.

It should be apparent that the number, type, function, and location of electrodes 95, 95' may be altered while remaining within the scope of the present invention. For example, only upper tray 10" may have electrodes 95 located thereon and/or electrodes 95, 95' may include a wire for communicating with the monitoring system. Electrodes 95, 95' may also be placed directly on the surface of upper moldable material 24, lower moldable material 54, or both. During the molding process the upper moldable material 24 or lower moldable material 54 is typically moved outward, i.e., toward the intraoral surfaces of the user's oral cavity as the teeth engage the moldable material. This outward movement of upper moldable material 24 and/or lower moldable material 54 serves to contact the electrode with the intraoral surfaces of the user's oral cavity so that no other electrode placement devices are needed. Nevertheless, the present invention also contemplates using electrode placement devices, such as springs and support members, to ensure that the electrodes 95, 95' are engaged with the intraoral surfaces of the user. Furthermore, it is contemplated that other patient monitoring devices (e.g., vibration monitoring devices, sound monitoring devices, etc.) and/or components may be employed in conjunction with oral appliance 1".

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An oral appliance system, comprising:
   an upper tray adaptable to conform to a user's maxillary dentition; and
   a plurality of lower trays, each of the lower trays adaptable to conform to the user's mandibular dentition, wherein at least some of the lower trays include an engagement member structured to engage the upper tray, wherein each engagement member is fixedly positioned in a different relative position with respect to each lower tray and wherein each of the lower trays are structured to impart a different fixed amount of mandibular advancement due to the different relative positioning of each of the engagement members.

2. The oral appliance system of claim 1, wherein the upper tray comprises: an upper moldable material; and an upper support member structured to define an upper region adapted to carry a portion of the upper moldable material.

3. The oral appliance system of claim 2, wherein the upper support member includes a base with a bonding surface and an occlusal surface, an outer wall with a front surface and a rear surface, and an inner wall with a front surface and a rear surface, and wherein at least a portion of the upper region is defined by the bonding surface of the base, the rear surface of the outer wall, and the front surface of the inner wall.

4. The oral appliance system of claim 3, wherein the bonding surface of the upper support member is concave to accommodate the Curve of Spee of a user's maxillary dentition.

5. The oral appliance system of claim 1, wherein the upper tray has a slotted engagement member extending therefrom and each of at least some of the lower trays has an elongated engagement member extending therefrom, and wherein the slotted engagement member is structured to receive the elongated engagement member of a selected one of the lower trays and releasably couple the upper tray to the selected one of the lower trays.

6. The oral appliance system of claim 5, wherein the slotted engagement member and the elongated engagement member cooperate to permit a predetermined amount of lateral movement and a predetermined amount of vertical movement of the upper tray relative to the selected one of the lower trays.

7. The oral appliance system of claim 6, wherein the predetermined amount of vertical movement is at least approximately 0.1 millimeter.

8. The oral appliance system of claim 7, wherein the predetermined amount of lateral movement is approximately between 10 millimeters and 13 millimeters.

9. The oral appliance system of claim 5, wherein the upper tray has a single slotted engagement member extending from the occlusal surface of the base of the upper support member and wherein the at least some of the lower trays has an elongated engagement member extending from the occlusal surface of the base of the lower support member.

10. The oral appliance system of claim 5, wherein at least one of the slotted engagement member and the elongated engagement member includes a frangible portion.

11. The oral appliance system of claim 1, wherein the upper tray includes an upper moldable material with a channel structured to align the user's dentition within the center thereof, the channel including a substantially V-shaped portion structured to engage an anterior portion of the user's maxillary dentition and a substantially U-shaped portion structured to engage a posterior portion of the user's maxillary dentition, and wherein at least one of the plurality of lower trays includes a lower moldable material with a channel structured to align the user's dentition within the center thereof, the channel including a substantially V-shaped portion structured to engage an anterior portion of the user's mandibular dentition and a substantially U-shaped portion structured to engage a posterior portion of the user's mandibular dentition.

12. The oral appliance system of claim 11, wherein at least one of the upper moldable material and the lower moldable material includes an ethylene-vinyl acetate copolymer resin and an aliphatic polyester.

13. The oral appliance system of claim 1, wherein each of the lower trays comprises: an lower moldable material; and a lower support member structured to define a lower region adapted to carry a portion of the lower moldable material.

14. The oral appliance system of claim 13, wherein the lower support member includes a base with a bonding surface and an occlusal surface, an outer wall with a front surface and a rear surface, and an inner wall with a front surface and a rear surface, and wherein at least a portion of the lower region is defined by the bonding surface of the base, the rear surface of the outer wall, and the front surface of the inner wall.

15. The oral appliance system of claim 14, wherein the bonding surface of the lower support member is convex to accommodate the Curve of Spee of a user's mandibular dentition.

16. The oral appliance system of claim 1, wherein each of the lower trays, in combination with the upper tray, are structured to impart an amount of vertical spacing between the user's maxillary dentition and mandibular dentition.

17. The oral appliance system of claim 16, wherein at least one of the lower trays, in combination with upper tray, is structured to impart approximately 0.394 inches (10 millimeters) of vertical spacing.

18. The oral appliance system of claim 1 further comprising a holding tray structured to engage at least one of the upper tray and some of the plurality of lower trays.

19. A method for effecting the patency of a user's airway, comprising: providing an oral appliance assembly comprising an upper tray adaptable to conform to a user's maxillary dentition and a plurality of lower trays each adaptable to conform to the user's mandibular dentition, wherein each of at least some of the lower trays is structured to couple with the upper tray to impart a different fixed amount of mandibular advancement; selecting of at least one of the plurality of lower trays; and coupling the upper tray with a selected one of the lower trays to form an oral appliance having a desired amount of mandibular advancement.

20. The method of claim 19, wherein providing an oral appliance assembly, further comprises: providing an upper tray having an upper moldable material and an upper support member structured to define an upper region adapted to carry a portion of the upper moldable material; and providing a lower tray having a lower moldable material and a lower support member structured to define lower region adapted to carry a portion of the lower moldable material.

21. The method of claim 20, wherein at least one of providing an oral appliance assembly, further comprises at least one of: providing a number of electrodes extending from at least one of the upper support member, lower support member, the upper moldable material, and the lower moldable; and structuring at least one of the upper support member and the lower support member to couple with and stabilize a patient interface device.

22. The method of claim 19, further comprising inserting the upper tray and the selected lower tray into the user's mouth.

23. The method of claim 19, wherein providing an oral appliance assembly includes at least one of fitting the upper tray to conform to a user's maxillary dentition and fitting at least one of the lower trays to a user's mandibular dentition.

24. The method of claim 19, wherein providing an oral appliance assembly, further comprises providing an upper tray and a lower tray which when engaged are structured to impart a desired amount of vertical spacing between the user's maxillary dentition and mandibular dentition.

25. The method of claim 19, wherein providing an oral appliance assembly, further comprises providing an upper tray and a lower tray which when engaged are structured to impart approximately 0.394 inches (10 millimeters) of vertical spacing between the user's maxillary dentition and mandibular dentition.

* * * * *